(12) United States Patent
Deinhammer et al.

(10) Patent No.: US 11,840,718 B2
(45) Date of Patent: *Dec. 12, 2023

(54) PROCESSES FOR PRODUCING ETHANOL

(71) Applicant: NOVOZYMES A/S, Bagsvaerd (DK)

(72) Inventors: Randy Deinhammer, Wake Forest, NC (US); Suzanne Clark, Youngsville, NC (US); Mauricio Quiros, Raleigh, NC (US); John Matthews, Louisburg, NC (US); Anne Glud Hjulmand, Raleigh, NC (US); Chee-Leong Soong, Raleigh, NC (US); Tomoko Matsui, Chiba (JP); Shinobu Takagi, Chiba (JP)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/052,080

(22) Filed: Nov. 2, 2022

(65) Prior Publication Data

US 2023/0265462 A1 Aug. 24, 2023

Related U.S. Application Data

(63) Continuation of application No. 17/036,601, filed on Sep. 29, 2020, now Pat. No. 11,566,266, which is a continuation of application No. 16/407,840, filed on May 9, 2019, now Pat. No. 10,941,422, which is a continuation of application No. 15/727,952, filed on Oct. 9, 2017, now Pat. No. 10,947,567, which is a continuation of application No. 13/994,310, filed as application No. PCT/US2011/066559 on Dec. 21, 2011, now Pat. No. 9,816,112.

(60) Provisional application No. 61/566,373, filed on Dec. 2, 2011, provisional application No. 61/426,039, filed on Dec. 22, 2010.

(51) Int. Cl.
| | |
|---|---|
| *C12P 7/06* | (2006.01) |
| *C12P 19/02* | (2006.01) |
| *C12P 19/14* | (2006.01) |
| *C12P 19/20* | (2006.01) |

(52) U.S. Cl.
CPC ......... *C12P 7/06* (2013.01); *C12Y 302/01001* (2013.01); *C12Y 302/01003* (2013.01); *C12Y 304/24* (2013.01); *C12P 19/02* (2013.01); *C12P 19/14* (2013.01); *C12P 19/20* (2013.01); *Y02E 50/10* (2013.01)

(58) Field of Classification Search
None
See application file for complete search history.

(56) References Cited

U.S. PATENT DOCUMENTS

| | | |
|---|---|---|
| 5,192,677 A | 3/1993 | Kinsella et al. |
| 5,705,379 A | 1/1998 | Wilson et al. |
| 5,756,339 A | 5/1998 | Mitta et al. |
| 6,358,726 B1 | 3/2002 | Takakura |
| 7,601,858 B2 | 10/2009 | Cantrell |
| 7,608,729 B2 | 10/2009 | Winsness et al. |
| 7,820,419 B2 | 10/2010 | Smith et al. |
| 8,008,517 B2 | 8/2011 | Cantrell et al. |
| 8,048,657 B2 | 11/2011 | Breneman |
| 9,677,095 B2 | 6/2017 | Deinhammer |
| 9,816,112 B2 * | 11/2017 | Deinhammer ....... C12Y 304/24 |
| 9,951,364 B2 | 4/2018 | Kang |
| 10,035,973 B2 | 7/2018 | Kreel |
| 10,093,882 B2 | 10/2018 | Clark |
| 10,731,104 B2 | 8/2020 | Kreel et al. |
| 10,781,398 B2 | 9/2020 | Kreel et al. |
| 10,844,318 B2 | 11/2020 | Clark et al. |
| 10,920,172 B2 | 2/2021 | Kreel et al. |
| 10,941,422 B2 * | 3/2021 | Deinhammer ............ C12P 7/06 |
| 10,947,567 B2 * | 3/2021 | Deinhammer .............................. C12Y 302/01003 |
| 11,499,170 B2 * | 11/2022 | Deinhammer .............................. C12Y 302/01001 |
| 11,505,765 B2 | 11/2022 | Kreel et al. |
| 11,566,266 B2 * | 1/2023 | Deinhammer ............ C12P 7/06 |
| 2002/0086402 A1 | 7/2002 | Takakura et al. |
| 2004/0057944 A1 | 3/2004 | Galle et al. |
| 2004/0219649 A1 | 11/2004 | Olsen |
| 2005/0084934 A1 | 4/2005 | Takakura |
| 2005/0100996 A1 | 5/2005 | Lantero, Jr. |
| 2007/0178567 A1 | 8/2007 | Lewis |
| 2007/0184150 A1 | 8/2007 | Bhargava |
| 2008/0138871 A1 | 6/2008 | Smith |
| 2009/0227004 A1 | 9/2009 | Dale |
| 2010/0058649 A1 | 3/2010 | Bootsma |
| 2012/0040436 A1 | 2/2012 | Harada |
| 2012/0214197 A1 | 8/2012 | Landvik |

(Continued)

FOREIGN PATENT DOCUMENTS

| | | |
|---|---|---|
| CN | 154717 | 7/1997 |
| CN | 1189188 | 7/1998 |

(Continued)

OTHER PUBLICATIONS

Anonymous_2006-2007_Biochemicals_reagents_and_kits_of_life_science_research.
Anonymous_2019_Danisco_petition_fro_inter_partes_review_of_US_10_035_973.
Ben_2010_Uniport_Access_No. Q9KWY6.
Brock_1967_Science_158(3804)_1012-1019, 1012-1019.
Bruins_2001_Appl_Biochem_Biotechnol_90_155-186, 155-186, 90.
Cheng 2011 Appl Biochem Biotechnol 163(6) 693-706, 693-706, 163(6).

(Continued)

*Primary Examiner* — Christian L Fronda
(74) *Attorney, Agent, or Firm* — David Fazzolare

(57) ABSTRACT

The present invention relates to processes for producing fermentation products from starch-containing material, wherein a thermostable alpha-amylase and optionally a thermostable protease are present and/or added during liquefaction. The invention also relates to a composition suitable for use in a process of the invention.

20 Claims, 5 Drawing Sheets

Specification includes a Sequence Listing.

(56) References Cited

U.S. PATENT DOCUMENTS

2014/0024064 A1 1/2014 Burlew
2014/0315243 A1 10/2014 Deinhammer et al.

FOREIGN PATENT DOCUMENTS

| | | |
|---|---|---|
| CN | 1260002 A | 7/2000 |
| CN | 1657614 A | 8/2005 |
| CN | 101115843 A | 1/2008 |
| CN | 101432433 A | 5/2009 |
| CN | 100564534 C | 12/2009 |
| CN | 101939421 A | 1/2011 |
| CN | 20120040436 A | 2/2012 |
| CN | 102834521 A | 12/2012 |
| CN | 102884183 A | 1/2013 |
| CN | 20120214197 A | 1/2013 |
| DE | 102005062984 A1 | 12/2005 |
| WO | 1992002614 A1 | 2/1992 |
| WO | 1992020777 A1 | 11/1992 |
| WO | 1997029179 A1 | 8/1997 |
| WO | 1998056926 A1 | 12/1998 |
| WO | 1999019467 A1 | 4/1999 |
| WO | 2002074895 A2 | 9/2002 |
| WO | 2003048353 A1 | 6/2003 |
| WO | 2004080923 A2 | 9/2004 |
| WO | 2004087889 A1 | 10/2004 |
| WO | 2005052146 A2 | 6/2005 |
| WO | 2005052161 A2 | 6/2005 |
| WO | 2005113785 A2 | 12/2005 |
| WO | 2006086792 A2 | 8/2006 |
| WO | 2007098396 A2 | 8/2007 |
| WO | 2007056321 A1 | 5/2008 |
| WO | 2009052101 A1 | 4/2009 |
| WO | 2009100138 A2 | 8/2009 |
| WO | 2010008841 A2 | 1/2010 |
| WO | 2011068803 A1 | 6/2011 |
| WO | 2011072191 A2 | 6/2011 |
| WO | 2011080353 A1 | 7/2011 |
| WO | 2011082425 A2 | 7/2011 |
| WO | 2011126897 A2 | 10/2011 |
| WO | 2011127802 A1 | 10/2011 |
| WO | 2012084225 A1 | 6/2012 |
| WO | 2012088303 A2 | 6/2012 |
| WO | 2013006756 A2 | 1/2013 |
| WO | 2013082486 A1 | 6/2013 |
| WO | 2018118815 A1 | 6/2018 |
| WO | 2018169780 A1 | 9/2018 |

OTHER PUBLICATIONS

Chica et al., Curr Op Biotechnol, 2005, 378-384, 16(4).
Clark_2020_Declaration_for_IPR_2020-00464, 2020-00464.
Connaris_1991_J_Gen_Microbiol_137_1193-1199, 1193-1199, 137.
Goode_2003_Journal_Am._Soc._Brew._Chem_61(2)_69-78.
Gray_1986_Uniprot_access_No. P00799.
Jacques 2003 Foreword Chapters 1 2 14 15, 1 2 14 15.
Katrolia_2012_Bioresource_Technology_110_578-586, 578-586, 110.
Kristjansson 1990 Biochem J 270 51-55, 51-55, 270.
Lao 1996 Appl Environ Microbiol 62(11) 4256-4259, 4256-4259, 62(11).
Lao_1998_Uniprot_access_No. O86984.
Li (Ed), 2010, Tianjin Science and Technology Translation Publishing Company, 26-28—Tr.
Li_(Ed)_2010_Tianjin_Science_and_Technology_Translation_Publishing_Company_26-28.
Little_1994_Ferment_7(3)_163-168, 163-168.
Maeder_2002_Uniprot_accession_No. Q8U0C9.
Majoni et al., Majoni 2011 Jaocs 88(4) 523-532 Danisco IPR, J Am Oil Chem Soc, 2011, 523-532, 88(4).
Niehaus_1999_Appl_Microbiol_Biotechnol_51_711-729, 711-729, 51.
Perez-Carillo_2012_Biochem_Eng_J_67_1-9, 67.
Prakash_2013_Biomed_research_international_Article_ID_264020_1-8.
Qi_2011_Zhengzhou_university_press_118-119, 118-119.
Qi_2011_Zhengzhou_university_press_118-119_Tr, 118-119.
Sen 2007 Appl Biochem Biotechnol 143(3) 212-223, 212-223, 143(3).
Silva_1998_Uniprot_accession_No. O31193.
Singh et al., Current Protein and Peptide Science, 2017, 1-11, 18.
Sun 2013 Food Safety 34(2) 72-77, 72-77, 34(2).
Thomas 1990 Appl Environ Microbiol 56(7) 2046-2050, 2046-2050, 56(7).
U.S. Pat. No. 10,035,973—PTAB decision granting IPR petition.
U.S. Pat. No. 14,362,002—OAs dated May 24, 2016, Jan. 17, 2017, Mar. 9, 2018, Sep. 19, 2018, Sep. 9, 2019.
U.S. Pat. No. 7,820,419—IPR 202000464 Institution Decision dated Jul. 28, 2020.
U.S. Pat. No. 7,820,419—No. IPR202000464 filed on Jan. 27, 2020.
Vielle 2001 Microbiol Mol Biol Revs 65(1) 1-43, 65(1).
Vijay_2019_Declaration.
Wang et al., J Agric Food Chem, 2009, 2302-2307, 57(6).
Wang_2008_Lipid_technology_20(9)_203-207, 203-207.
Ward_2002_Archaea_1_63-74, 63-74, 1.
WO—2003048353A1—Access No. ABR62336.
WO—2011127802A1—Accession No. AZN72409.
Yang (Ed), 2013, Industrial patent analysis report, Intellectual property press 16, 79.
Yang (Ed), 2013, Industrial patent analysis report, Intellectual property press 16, 79—Tr.
Yao_2014_Journal_of_bioprocess_engineering_and_biorefinery_3_323-331, 323-331, 3.
Zheng_(Ed)_2003_Science_and_Technology_Literature_Press_96.
Zheng_(Ed)_2003_Science_and_Technology_Literature_Press_96_Tr.
Zheng_(Ed)_2009_Zhongshan_University_Press_315.
Zheng_(Ed)_2009_Zhongshan_University_Press_315_Tr.
Fed. Cir. Case: 21-2184 re Rule 36 Affirmance of IPR 2020-00464 Final Written Decision dated Oct. 5, 2022.
IPR 2020-00464 re U.S. Pat. No. 7,820,419 B2—Final Written Decision dated Jul. 20, 2021.
IPR 2019-01010 re U.S. Pat. No. 10,035,973 B2—Granting Request for Adverse Judgment After Institution of Trial.

* cited by examiner

PROCESSES FOR PRODUCING ETHANOL

CROSS-REFERENCE TO RELATED APPLICATIONS

This application is a continuation of U.S. application Ser. No. 17/072,557 filed Sep. 29, 2020, now U.S. Pat. No. 11,499,170 granted Nov. 15, 2022 which is a continuation of U.S. application Ser. No. 16/407,840 filed May 9, 2019, now U.S. Pat. No. 10,941,422 granted Mar. 9, 2021, which is a continuation of U.S. application Ser. No. 15/727,952 filed Oct. 9, 2017, now U.S. Pat. No. 10,947,567 granted Mar. 16, 2021, which is a continuation of U.S. application Ser. No. 13/994,310 filed Oct. 1, 2013, now U.S. Pat. No. 9,816,112 granted Nov. 14, 2017, which is a 35 U.S.C. 371 national application of PCT/US2011/066559 filed Dec. 21, 2011 which claims priority or the benefit under 35 U.S.C. 119 of U.S. provisional application Nos. 61/426,039 and 61/566,373 filed Dec. 22, 2010 and Dec. 2, 2011, respectively, the contents of which are fully incorporated herein by reference.

FIELD OF THE INVENTION

The present invention relates to processes for producing fermentation products from starch-containing material. The invention also relates to a composition suitable for use in a process of the invention.

REFERENCE TO A SEQUENCE LISTING

This application contains a Sequence Listing in computer readable form. The contents of the electronic sequence listing created on May 16, 2023, named SQ ST26.xml and 30 KB in size, is hereby incorporated by reference in its entirety.

BACKGROUND OF THE INVENTION

Production of fermentation products, such as ethanol, from starch-containing material is well-known in the art. Industrially two different kinds of processes are used today. The most commonly used process, often referred to as a "conventional process", including liquefying gelatinized starch at high temperature using typically a bacterial alpha-amylase, followed by simultaneous saccharification and fermentation carried out in the presence of a glucoamylase and a fermentation organism. Another well known process, often referred to as a "raw starch hydrolysis"-process (RSH process) includes simultaneously saccharifying and fermenting granular starch below the initial gelatinization temperature typically in the presence of an acid fungal alpha-amylase and a glucoamylase.

Despite significant improvement of fermentation product production processes over the past decade a significant amount of residual starch material is not converted into the desired fermentation product, such as ethanol. At least some of the unconverted residual starch material, e.g., sugars and dextrins, is in the form of non-fermentable Maillard products.

Therefore, there is still a desire and need for providing processes for producing fermentation products, such as ethanol, from starch-containing material that can provide a higher fermentation product yield compared to a conventional process.

SUMMARY OF THE INVENTION

The present invention relates to processes of producing fermentation products, such as ethanol from starch-containing material using a fermenting organism. The invention also relates to a composition suitable for use in a process of the invention.

In the first aspect the invention relates to processes for producing fermentation products, such as ethanol, from starch-containing material comprising the steps of:
  i) liquefying the starch-containing material at a pH in the range from 4.5-5.0 at a temperature in the range from 80-90° C. using:
    an alpha-amylase having a T½ (min) at pH 4.5, 85° C., 0.12 mM $CaCl_2$) of at least 10;
    optionally a protease having a thermostability value of more than 20% determined as Relative Activity at 80° C./70° C.;
  ii) saccharifying using a carbohydrate-source generating enzyme;
  iii) fermenting using a fermenting organism.

In an embodiment a carbohydrate-source generating enzyme, in particular a thermostable glucoamylase, and/or a pullulanase is(are) present and/or added during liquefaction in step i).

In a second aspect the invention relates to compositions comprising an alpha-amylase and a protease, wherein
  i) the alpha-amylase has a T ½(min) at pH 4.5, 85° C., 0.12 mM $CaCl_2$) of at least 10; and
  ii) the protease has a thermostability value of more than 20% determined as Relative Activity at 80° C./70° C.

In an embodiment the composition further comprises a carbohydrate-source generating enzyme, in particular a thermostable glucoamylase, and/or a pullulanase.

In an embodiment a second alpha-amylase is present and/or added during liquefaction step i).

In an embodiment the invention relates to a composition comprising:
  i) an alpha-amylase having a T½ (min) at pH 4.5, 85° C., 0.12 mM $CaCl_2$) of at least 10 derived from *Bacillus stearothermophilus;*
  ii) a protease having a thermostability value of more than 20% determined as Relative Activity at 80° C./70° C. derived from *Pyrococcus furiosus* and/or *Thermoascus aurantiacus;* and optionally
  iii) a glucoamylase derived from *Penicillium oxalicum.*

In an embodiment the composition comprises a second alpha-amylase.

Alpha-Amylase A (0.35 micro g)+Alpha-Amylase 1407 (1.4 micro g)+Glucoamylase PE001 (10 micro g)+Protease 196 (1 micro g) (pH 4.8);

Alpha-Amylase A (0.7 micro g)+Alpha-Amylase 1407 (1.4 micro g)+Glucoamylase PE001 (10 micro g)+Protease 196 (1 micro g) (pH 4.8).

Figure 4:
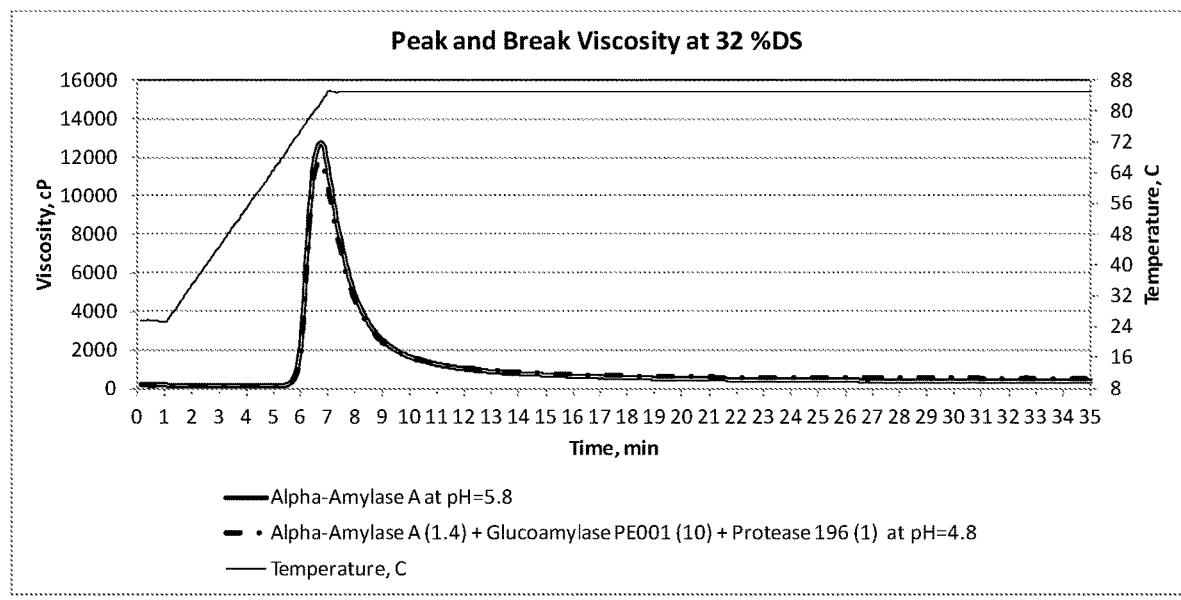

FIG. 4 shows the peak and break viscosity at 32% DS for the experiment in Example 10 comparing Alpha-Amylase A (1.4 micro g) (pH 5.8) and Alpha-Amylase A (1.4 micro g)+Glucoamylase PE001 (10 micro g)+Protease 196 (1 micro g) (pH 4.8).

Figure 5:
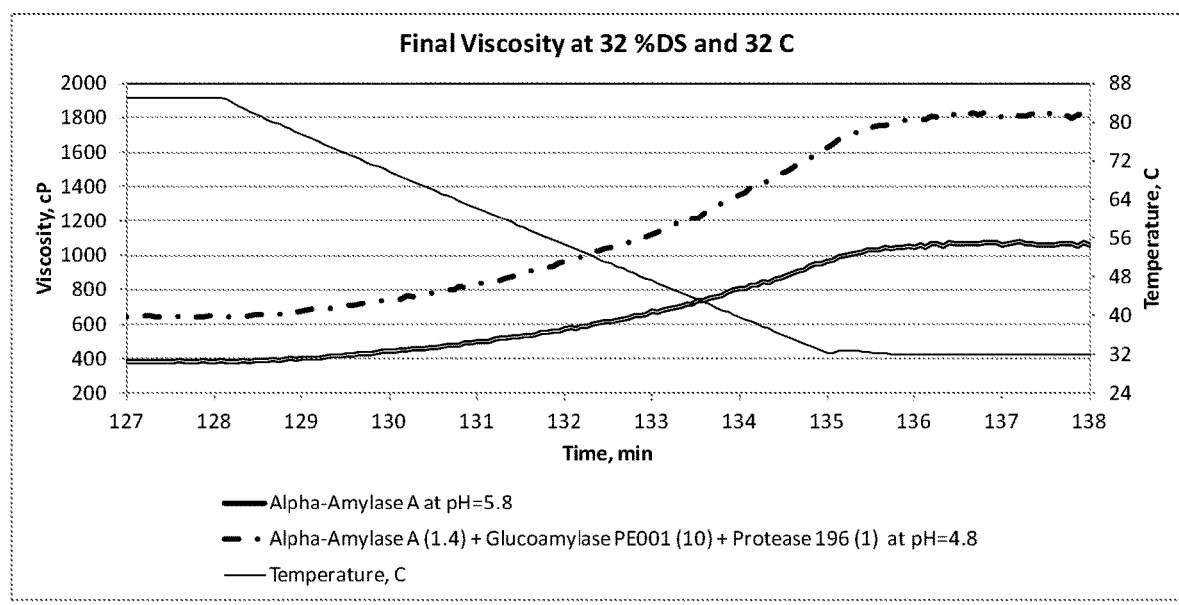

FIG. 5 shows the final viscosity at 32% DS, at 32° C. for the experiment in Example 10 comparing Alpha-Amylase A (1.4 micro g) (pH 5.8) and Alpha-Amylase A (1.4 micro g)+Glucoamylase PE001 (10 micro g)+Protease 196 (1 micro g) (pH 4.8).

DETAILED DESCRIPTION OF THE INVENTION

The present invention relates to processes of producing fermentation products, such as ethanol from starch-containing material using a fermenting organism. The invention also relates to a composition suitable for use in a process of the invention.

The inventors have shown that a process of the invention has a number of advantages. As shown in the Examples a process of the invention results in a higher ethanol yield. Other benefits, includes a reduced need for using $H_2SO_4$ for pH adjustment. This results in less sulfur downstream in the DDGS, less front-end fouling, less beerstone, and less phytate precipitation.

A process of the invention also results in reduced loss of sugars and dextrins to Maillard products. The DDGS color is improved and the heat exchanger lifetime (less solids) is extended. Furthermore, due to the higher thermostability of the enzymes used the enzyme dose may be reduced. A process of the invention requires limited changes to existing process and process equipment and thus limited capital investment.

By having a thermostable alpha-amylase and a second alpha-amylase as defined herein in liquefaction the peak viscosity, e.g., in slurry tank is (further) reduced. This result in less energy spent for mixing. Also having a lower average viscosity improves the mixing of the mash/starch in the slurry tank and its pumping through the liquefaction process.

In the first aspect the invention relates to processes for producing fermentation products from starch-containing material comprising the steps of:
i) liquefying the starch-containing material at a pH in the range from 4.5-5.0 at a temperature in the range from 80-90° C. using:
   an alpha-amylase having a T½ (min) at pH 4.5, 85° C., 0.12 mM $CaCl_2$) of at least 10;
   optionally a protease having a thermostability value of more than 20% determined as Relative Activity at 80° C./70° C.;
ii) saccharifying using a carbohydrate-source generating enzyme;
iii) fermenting using a fermenting organism.

In a preferred embodiment step ii) and iii) are carried out either sequentially or simultaneously. The thermostable alpha-amylase and optionally a thermostable protease and optionally the carbohydrate-source generating enzyme, preferably thermostable glucoamylase, and/or optionally a pullulanase may be added before and/or during liquefaction step i). Examples of thermostable alpha-amylases can be found in the "Alpha-Amylase Present and/or Added During Liquefaction" section below. Examples of thermostable proteases can be found in the "Protease Present and/or Added During Liquefaction"-section below. A composition of the invention may suitably be used in a process of the invention. However, the enzyme components may also be added separately.

In a preferred embodiment the pH during liquefaction is between 4.5-4.8.

In an embodiment a carbohydrate-source generating enzyme is also present during liquefaction. In a preferred embodiment the carbohydrate-source generating enzymes is a thermostable glucoamylase. In an embodiment the carbohydrate-source generating enzyme is different from the one used during saccharification in step ii) and/or fermentation in step iii).

Examples of "carbohydrate-source generating enzymes", including in particular glucoamylases, can be found in the "Carbohydrate-Source Generating Enzyme Present and/or Added During Liquefaction"-section below. Examples of thermostable glucoamylases can be found in the "Glucoamylase Present and/or Added During Liquefaction"-section below.

In an embodiment, the process of the invention further comprises, prior to the step i), the steps of:
a) reducing the particle size of the starch-containing material, preferably by dry milling;
b) forming a slurry comprising the starch-containing material and water.

The starch-containing starting material, such as whole grains, may be reduced in particle size, e.g., by milling, in order to open up the structure and allowing for further processing. Generally there are two types of processes: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing. According to the invention dry milling is preferred. In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

The aqueous slurry may contain from 10-55 w/w-% dry solids (DS), preferably 25-45 w/w-% dry solids (DS), more preferably 30-40 w/w-% dry solids (DS) of starch-containing material. The slurry is heated to above the gelatinization temperature, preferably for between 80-90° C., pH 4.5-4.8 for around 15-60 minutes.

The thermostable alpha-amylase, optional thermostable protease and optional carbohydrate-source generating enzyme, in particular thermostable glucoamylase, and/or optional pullulanase may be added to the aqueous slurry to initiate liquefaction (thinning). In an embodiment only a part of the enzyme blend (composition of the invention) is added to the aqueous slurry, while the rest of the enzyme is added during liquefaction step i). Liquefaction step i) is typically carried out at 80-90° C., pH 4.5-4.8 for 1-3 hours.

The aqueous slurry may in an embodiment be jet-cooked to further gelatinize the slurry before being subjected to liquefaction in step i). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

Saccharification and Fermentation

One or more carbohydrate-source generating enzymes, in particular glucoamylases, are present and/or added during saccharification step ii) and/or fermentation step iii). The carbohydrate-source generating enzyme may preferably be a glucoamylase, but may also be an enzyme selected from the group consisting of: beta-amylase, maltogenic amylase and alpha-glucosidase.

Examples of carbohydrate-source generating enzyme, including glucoamylases, can be found in the "Carbohydrate-Source Generating Enzyme Present and/or Added During Saccharification and/or Fermentation"-section below.

When doing sequential saccharification and fermentation the saccharification step ii) may be carried out using conditions well-known in the art. For instance, the saccharification step ii) may last up to from about 24 to about 72 hours, however, it is common to do only a pre-saccharification of typically 40-90 minutes at a temperature between 30-65° C., typically about 60° C., followed by saccharification during fermentation in simultaneous saccharification and fermentation ("SSF"). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step ii) and the fermentation step iii) are carried out simultaneously. There is no holding stage for the saccharification, meaning that a fermenting organism, such as yeast, and enzyme(s), may be added together. SSF are according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 3.5-5, in particular between 3.8 and 4.3.

Fermentation Medium

"Fermentation media" or "fermentation medium" which refers to the environment in which fermentation is carried out and which includes the fermentation substrate, that is, the carbohydrate source that is metabolized by the fermenting organism. The fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms

The term "Fermenting organism" refers to any organism, including bacterial and fungal organisms, suitable for use in a fermentation process and capable of producing the desired fermentation product. Especially suitable fermenting organisms are able to ferment, i.e., convert, sugars, such as glucose or maltose, directly or indirectly into the desired fermentation product, such as ethanol. Examples of fermenting organisms include fungal organisms, such as yeast. Preferred yeast includes strains of *Saccharomyces* spp., in particular, *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Starch-Containing Materials

Any suitable starch-containing material may be used according to the present invention. The starting material is generally selected based on the desired fermentation product. Examples of starch-containing materials, suitable for use in a process of the invention, include whole grains, corn, wheat, barley, rye, milo, sago, cassava, tapioca, sorghum, rice, peas, beans, or sweet potatoes, or mixtures thereof or starches derived there from, or cereals. Contemplated are also waxy and non-waxy types of corn and barley.

Fermentation Products

The term "fermentation product" means a product produced by a process including a fermentation step using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may preferably be used as fuel, that typically is blended with gasoline. However, in the case of ethanol it may also be used as potable ethanol.

Recovery

Subsequent to fermentation the fermentation product may be separated from the fermentation medium. The slurry may be distilled to extract the desired fermentation product. Alternatively the desired fermentation product may be extracted from the fermentation medium by micro or membrane filtration techniques. The fermentation product may also be recovered by stripping or other method well known in the art.

Alpha-Amylase Present and/or Added During Liquefaction

According to the invention a thermostable alpha-amylase is present and/or added during liquefaction optionally together with a thermostable protease, and optionally a carbohydrate-source generating enzyme, preferably a thermostable glucoamylase, and/or optionally a pullulanase. According to the invention the alpha-amylase has high activity toward starch solubilisation in liquefaction at pH 4.5 to 5.0 and high thermostability at pH 4.5-5.0 and 80-90° C., preferably 4.5-4.8, around 85° C.

More specifically the alpha-amylase used in a process of the invention has a T½ (min) at pH 4.5, 85° C., 0.12 mM $CaCl_2$ of at least 10 determined as described in Example 1.

In a preferred embodiment T½ (min) at pH 4.5, 85° C., 0.12 mM CaCl$_2$, is at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the thermostable alpha-amylase is a *Bacillus stearothermophilus* alpha-amylase variant having at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 or SEQ ID NO: 1 herein with the double deletion I181+G182 and substitution N193F, further comprising the following mutations:

alpha-amylase may be less thermostable and/or less efficient at pH 4.5, 85° C., 0.12 mM CaCl$_2$, or around pH 4.8, than a thermostable alpha-amylase defined herein added and/or present during liquefaction according to the invention.

In an embodiment the second alpha-amylase is of bacterial origin.

In an embodiment the second alpha-amylase is derived from a strain of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein. The second alpha-amylase may be a truncated *Bacillus stearothermophilus* alpha-amylase, preferably to have around 491 amino acids.

In an embodiment second alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;
V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
V59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q + Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V.

The thermostable alpha-amylase may be a truncated *Bacillus stearothermophilus* alpha-amylase, preferably to have around 491 amino acids.

Second Alpha-Amylase Present and/or Added During Liquefaction

When a second alpha-amylase is present and/or added during liquefaction step i) a positive viscosity reducing effect is obtained. As can be seen from Example 10 the combination of a thermostable alpha-amylase (e.g., Alpha-Amylase BE1407) with or without the presence of a thermostable protease (e.g., Protease 196) and thermostable glucoamylase (e.g., Glucoamylase PO) and further a second alpha-amylase (e.g. Alpha-amylase A) results in decrease peak viscosity and final viscosity.

Therefore, in this aspect of the invention a second alpha-amylase is added during liquefaction step i). The second In an embodiment the second alpha-amylase has a T½ (min) at pH 4.5, 85° C., 0.12 mM CaCl$_2$) of below 10 determined as described in Example 1.

In an embodiment the second alpha-amylase has a T½ (min) at pH 4.5, 85° C., 0.12 mM CaCl$_2$) of below 8, such as below 7, such as below 6, such as below 5.

In an embodiment the second alpha-amylase has a T½ (min) at pH 4.5, 85° C., 0.12 mM CaCl$_2$) between 2 and 10, such as between 3 and 8, such as above 4 to 10, such as above 4 to 8.

In an embodiment the second alpha-amylase may be derived from *Bacillus stearothermophilus* and may have the following mutations: I181*+G182* or I181*+G182*+N193F (using SEQ ID NO: 1 for numbering).

In an embodiment the invention relates to a process for producing fermentation products from starch-containing material comprising the steps of:

i) liquefying the starch-containing material at a pH in the range from 4.5-5.0 at a temperature in the range from 80-90° C. using:
an alpha-amylase having a T½ (min) at pH 4.5, 85° C., 0.12 mM CaCl$_2$) of at least 10, and further a second alpha-amylase having a T½ (min) at pH 4.5, 85° C., 0.12 mM CaCl$_2$) of less than 10;
a protease having a thermostability value of more than 20% determined as Relative Activity at 80° C./70° C.;
ii) saccharifying using a glucoamylase;
iii) fermenting using a fermenting organism.

Protease Present and/or Added During Liquefaction

According to the invention a thermostable protease may be present and/or added during liquefaction together with a thermostable alpha-amylase, and optionally a carbohydrate-source generating enzyme, preferably a thermostable glucoamylase, and/or optionally a pullulanase.

A protease used in a process of the invention has either
i) a thermostability value of more than 20% determined as Relative Activity at 80° C./70° C.; and/or
ii) a thermostability value of more than 10% determined as Relative Activity at 85° C./70° C.

In an embodiment the protease has a thermostability value:
of more than 30%, more than 40%, more than 50%, more than 60%, more than 70%, more than 80%, more than 90% determined as Relative Activity at 80° C./70° C., and/or
of more than 12%, more than 14%, more than 16%, more than 18%, more than 20%, more than 25% determined as Relative Activity at 85° C./70° C.; and/or
of more that 20%, more than 30%, more than 40%, more than 50%, more than 60%, more than 70%, more than 80%, more than 90% determined as Remaining Activity at 80° C.; and/or
of more that 20%, more than 30%, more than 40%, more than 50%, more than 60%, more than 70%, more than 80%, more than 90% determined as Remaining Activity at 84° C. and/or.

Purified variants may have a themostability for above 90, above 100 at 85° C. as determined using the Zein-BCA assay as disclosed in Example 3.

Determination of "Relative Activity" and "Remaining Activity" is determined as described in Example 2.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used in a process of the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

In an embodiment the protease has at least 20%, such as at least 30%, such as at least 40%, such as at least 50%, such as at least 60%, such as at least 70%, such as at least 80%, such as at least 90%, such as at least 100% of the activity of the JTP196 protease variant or Protease Pfu determined by the AZCL-casein assay.

There are no limitations on the origin of the protease used in a process of the invention as long as it fulfills the thermostability properties defined above. The protease may be a variant of, e.g., a wild-type protease as long as the protease has the thermostability properties defined above. In a preferred embodiment the protease is a variant of a metallo protease as defined above. In an embodiment the protease used in a process of the invention is of fungal origin, such as a fungal metallo protease, such as a fungal metallo protease derived from a strain of the genus Thermoascus, preferably a strain of Thermoascus aurantiacus, especially Thermoascus aurantiacus CGMCC No. 0670 (classified as EC 3.4.24.39).

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO. 1 in WO 2010/008841 or SEQ ID NO: 3 herein.

In an embodiment the protease is a variant of the mature part of the metallo protease shown in SEQ ID NO: 2 disclosed in WO 2003/048353 or the mature part of SEQ ID NO: 1 in WO 2010/008841 and shown as SEQ ID NO: 3 herein with the following mutations:
S5*+N26R+D79L+S87P+A112P+D142L;
S5*+D79L+S87P+A112P+D142L;
N26R+T46R+D79L+S87P+A112P+D142L;
A27K+D79L+Y82F+S87G+D104P+A112P+A126V+D142L;
A27K+D79L+Y82F+D104P+A112P+A126V+D142L;
A27K+D79L+S87P+A112P+T124V+D142L;
A27K+D79L+S87P+A112P+A126V+D142L;
A27K+D79L+S87P+A112P+D142L;
A27K+Y82F+S87G+D104P+A112P+A126V+D142L;
A27K+Y82F+D104P+A112P+A126V+D142L;
S36P+D79L+S87P+A112P+D142L;
A37P+D79L+S87P+A112P+D142L;
S38T+D79L+S87P+A112P+A126V+D142L;
T46R+D79L+S87P+T116V+D142L;
S49P+D79L+S87P+A112P+D142L;
S50P+D79L+S87P+A112P+D142L;
S70V+D79L+Y82F+S87G+Y97W+A112P+D142L;
S70V+D79L+Y82F+S87G+A112P+D142L;
D79L+P81R+S87P+A112P+D142L;
D79L+Y82F+S87G+Y97W+D104P+A112P+D142L;
D79L+Y82F+S87G+D104P+A112P+D142L;
D79L+Y82F+S87G+A112P+A126V+D142L;
D79L+Y82F+S87G+A112P+D142L;
D79L+Y82F+S87P+A112P+T124V+D142L;
D79L+Y82F+S87P+A112P+A126V+D142L;

D79L+Y82F+S87P+A112P+D142L;
D79L+S87P+N98C+A112P+G135C+D142L;
D79L+S87P+D104P+A112P+D142L;
D79L+S87P+A112P+T124V+A126V+D142L;
D79L+S87P+A112P+T124V+D142L;
D79L+S87P+A112P+D142L;
D79L+S87P+A112P+D142L+T141C+M161C;
Y82F+S87G+S70V+D79L+D104P+A112P+D142L;
Y82F+S87G+D79L+D104P+A112P+A126V+D142L.

In an embodiment the thermostable protease present and/or added during liquefaction step i) is derived from a strain of *Pyrococcus*, such as a strain of *Pyrococcus furiosus*. In an embodiment the protease is one shown as SEQ ID NO: 1 in U.S. Pat. No. 6,358,726-B1 (Takara Shuzo Company). In another embodiment the protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Shuzo Co. Ltd, Japan.

The *Pyrococcus furiosus* protease is a thermostable protease. The commercial product *Pyrococcus furiosus* protease (Pfu S) was found to have a thermostability of 110% (80° C./70° C.) and 103% (90° C./70° C.) at pH 4.5 determined as described in Example 2 herein.

Carbohydrate-Source Generating Enzyme Present and/or Added During Liquefaction

According to the invention a carbohydrate-source generating enzyme, preferably a thermostable glucoamylase, is present and/or added during liquefaction together with a thermostable alpha-amylase and optionally a thermostable protease. As mentioned above a pullulanase may also be present and/or added during liquefaction step i).

The term "carbohydrate-source generating enzyme" includes any enzymes generating fermentable sugars. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrates may be converted directly or indirectly to the desired fermentation product, preferably ethanol. According to the invention a mixture of carbohydrate-source generating enzymes may be used. Specific examples include glucoamylase (being glucose generators), beta-amylase and maltogenic amylase (being maltose generators).

In a preferred embodiment the carbohydrate-source generating enzyme is a thermostable glucoamylase. The carbohydrate-source generating enzyme, in particular thermostable glucoamylase, may be added together with or separately from the thermostable alpha-amylase and optionally the thermostable protease.

In an embodiment the carbohydrate-source generating enzyme, preferably a thermostable glucoamylase, has a Relative Activity heat stability at 85° C. of at least 20%, at least 30%, preferably at least 35%. In an embodiment the carbohydrate-generating enzyme is a glucoamylase having a relative activity at pH 4.5 of at least 80%, preferably at least 85%, preferably at least 90%, preferably at least 95%.

In a specific and preferred embodiment the carbohydrate-source generating enzyme is a thermostable glucoamylase, preferably of fungal origin, preferably a filamentous fungi, such as from a strain of the genus *Penicillium*, especially a strain of *Penicillium oxalicum* disclosed as SEQ ID NO: 2 in PCT/CN10/071753 published as WO 2011/127802 (which is hereby incorporated by reference) and shown in SEQ ID NO: 9 or 14 herein.

In a preferred embodiment the carbohydrate-source generating enzyme is a variant of the *Penicillium oxalicum* glucoamylase disclosed as SEQ ID NO: 2 in PCT/CN10/071753 published as WO 2011/127802 and shown in SEQ ID NOS: 9 and 14 herein, having a K79V substitution (using the mature sequence shown in SEQ ID NO: 14 for numbering). The K79V glucoamylase variant has reduced sensitivity to protease degradation relative to the parent as disclosed in U.S. application No. 61/531,189 (which is hereby incorporated by reference).

In a specific embodiment the carbohydrate-source generating enzyme is a glucoamylase, preferably derived from a strain of the genus *Penicillium*, especially a strain of *Penicillium oxalicum* disclosed in PCT/CN10/071753 published as WO 2011/127802. The glucoamylase may also be glucoamylase having at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802 and shown as SEQ ID NO: 9 and 14 herein.

Pullulanase Present and/or Added During Liquefaction

Optionally a pullulanase may be present and/or added during liquefaction step i) together with a thermostable alpha-amylase and optionally a thermostable protease. As mentioned above a carbohydrate-source generating enzyme, preferably a thermostable glucoamylase, may also be present and/or added during liquefaction step i).

The pullulanase may be present and/or added during liquefaction step i) and/or saccharification step ii) or simultaneous saccharification and fermentation.

Pullulanases (E.C. 3.2.1.41, pullulan 6-glucano-hydrolase), are debranching enzymes characterized by their ability to hydrolyze the alpha-1,6-glycosidic bonds in, for example, amylopectin and pullulan.

Contemplated pullulanases according to the present invention include the pullulanases from *Bacillus amyloderamificans* disclosed in U.S. Pat. No. 4,560,651 (hereby incorporated by reference), the pullulanase disclosed as SEQ ID NO: 2 in WO 01/151620 (hereby incorporated by reference), the *Bacillus deramificans* disclosed as SEQ ID NO: 4 in WO 01/151620 (hereby incorporated by reference), and the pullulanase from *Bacillus acidopullulyticus* disclosed as SEQ ID NO: 6 in WO 01/151620 (hereby incorporated by reference) and also described in *FEMS Mic. Let.* 115: 97-106 (1994).

Additional pullulanases contemplated according to the present invention included the pullulanases from *Pyrococcus woesei*, specifically from *Pyrococcus woesei* DSM No. 3773 disclosed in WO 92/02614, and the mature protein sequence disclosed as SEQ ID No: 6 herein.

In an embodiment the pullulanase is a family GH57 pullulanase. In an embodiment the pullulanase includes an X47 domain as disclosed in U.S. 61/289,040 published as WO 2011/087836 (which are hereby incorporated by reference). More specifically the pullulanase may be derived from a strain of the genus *Thermococcus*, including *Thermococcus litoralis* and *Thermococcus hydrothermalis*, such as the *Thermococcus hydrothermalis* pullulanase shown in SEQ ID NO: 11 truncated at site X4 right after the X47 domain (i.e., amino acids 1-782 in SEQ ID NOS: 11 and 12 herein). The pullulanase may also be a hybrid of the *Thermococcus litoralis* and *Thermococcus hydrothermalis* pullulanases or a *T. hydrothermalis/T. litoralis* hybrid enzyme with truncation site X4 disclosed in U.S. 61/289,040 published as WO 2011/087836 (which is hereby incorporated by reference) and disclosed in SEQ ID NO: 12.

The pullulanase may according to the invention be added in an effective amount which include the preferred amount of about 0.0001-10 mg enzyme protein per gram DS, preferably 0.0001-0.10 mg enzyme protein per gram DS, more preferably 0.0001-0.010 mg enzyme protein per gram DS. Pullulanase activity may be determined as NPUN. An Assay for determination of NPUN is described in the "Materials & Methods"-section below.

Suitable commercially available pullulanase products include PROMOZYME D, PROMOZYME™ D2 (Novozymes A/S, Denmark), OPTIMAX L-300 (Genencor Int., USA), and AMANO 8 (Amano, Japan).

Carbohydrate-Source Generating Enzyme Present and/or Added During Saccharification and/or Fermentation According to the invention a carbohydrate-source generating enzyme, preferably a glucoamylase, is present and/or added during saccharification and/or fermentation.

In a preferred embodiment the carbohydrate-source generating enzyme is a glucoamylase, of fungal origin, preferably from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*.

Glucoamylase

According to the invention the glucoamylase present and/or added during saccharification and/or fermentation may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (*Agric. Biol. Chem.* 55(4): 941-949 (1991)), or variants or fragments thereof. Other *Aspergillus* glucoamylase variants include variants with enhanced thermal stability: G137A and G139A (Chen et al., 1996, Prot. Eng. 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in position A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and (Nagasaka et al., 1998, "Purification and properties of the raw-starch-degrading glucoamylases from *Corticium rolfsii*, *Appl. Microbiol. Biotechnol.* 50:323-330), *Talaromyces* glucoamylases, in particular derived from *Talaromyces emersonii* (WO 99/28448), *Talaromyces leycettanus* (US patent no. Re. 32,153), *Talaromyces duponti*, *Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831) and *Trametes cingulata*, *Pachykytospora papyracea*; and *Leucopaxillus giganteus* all disclosed in WO 2006/069289; or *Peniophora rufomarginata* disclosed in WO 2007/124285; or a mixture thereof. Also hybrid glucoamylase are contemplated according to the invention. Examples the hybrid glucoamylases disclosed in WO 2005/045018. Specific examples include the hybrid glucoamylase disclosed in Tables 1 and 4 of Example 1 (which hybrids are hereby incorporated by reference).

In an embodiment the glucoamylase is derived from a strain of the genus *Pycnoporus*, in particular a strain of *Pycnoporus* as described in U.S. 61/264,977 published as WO 2011/066576 (SEQ ID NO: 2, 4 or 6), or from a strain of the genus *Gloephyllum*, in particular a strain of *Gloephyllum* as described in U.S. 61/406,741 published as WO 2011/068803 (SEQ ID NO: 2, 4, 6, 8, 10, 12, 14 or 16) or a strain of the genus *Nigrofomes*, in particular a strain of *Nigrofomes* sp. disclosed in U.S. 61/411,044 or PCT/US10/058375 (SEQ ID NO: 2) (all references hereby incorporated by reference). Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to any one of the mature parts of the enzyme sequences mentioned above.

Contemplated are also glucoamylases which exhibit a high identity to any of above mention glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Glucoamylases may in an embodiment be added in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ ECXEL and AMG™ E (from Novozymes A/S); OPTIDEX™ 300, GC480, GC417 (from Genencor Int.); AMIGASE™ and AMIGASE™ PLUS (from DSM); G-ZYME™ G900, G-ZYME™ and G990 ZR (from Genencor Int.).

Maltogenic Amylase

The carbohydrate-source generating enzyme present and/or added during saccharification and/or fermentation may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference. The maltogenic amylase may in a preferred embodiment be added in an amount of 0.05-5 mg total protein/gram DS or 0.05-5 MANU/g DS.

A Composition Comprising Alpha-Amylase and Protease

A composition of the invention comprises a thermostable alpha-amylase and a thermostable protease. The composition may also optionally comprise a thermostable carbohydrate-source generating enzyme and optionally a pullulanase.

Therefore, in this aspect the invention relates to composition comprising an alpha-amylase and a protease, wherein the i) alpha-amylase has a T½ (min) at pH 4.5, 85° C., 0.12 mM CaCl$_2$) of at least 10;
ii) protease having a thermostability value of more than 20% determined as Relative Activity at 80° C./70° C.

The composition optionally further comprises a carbohydrate-source generating enzyme. Said carbohydrate-source generating enzyme may be a thermostable glucoamylase having a Relative Activity heat stability at 85° C. of at least 20%, at least 30%, preferably at least 35%.

The thermostable alpha-amylase is preferably a bacterial alpha-amylase, in particular of the genus *Bacillus*, such as a strain of *Bacillus stearothermophilus*, in particular a variant of a *Bacillus stearothermophilus* alpha-amylase, such as a variant of one shown in SEQ ID NO: 3 in WO 99/019467 or SEQ ID NO: 1 herein. Alpha-amylase variants are described further in the "Alpha-Amylase Present and/or Added During Liquefaction"-section above. The alpha-amylase may have a T½ (min) at pH 4.5, 85° C., 0.12 mM CaCl$_2$) of at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

In an embodiment the alpha-amylase is selected from the group of *Bacillus stearomthermphilus* alpha-amylase variants, in particular truncated to be 491 amino acids long, with mutations selected from the group of:

I181*+G182*+N193F+V59A+Q89R+E129V+K177L+R179E+H208Y+K220P+N224L+Q254S;

I181*+G182*+N193F+E129V+K177L+R179E; and

I181*+G182*+N193F+E129V+K177L+R179E+K220P+N224L+S242Q+Q254S (using SEQ ID NO: 1 herein for numbering).

It should be understood that these alpha-amylases are only specific examples. Any alpha-amylase disclosed above in the "Alpha-Amylase Present and/or Added During Liquefaction"-section above may be used as the alpha-amylase component in a composition of the invention.

The protease has a thermostability of:
i) more than 30%, more than 40%, more than 50%, more than 60%, more than 70%, more than 80%, more than 90% determined as Relative Activity at 80° C./70° C.; or
ii) more than 12%, more than 14%, more than 16%, more than 18%, more than 20%, more than 25% determined as Relative Activity at 85° C./70° C.

In an embodiment the protease is a variant of the metallo protease show in SEQ ID NO: 3 derived from *Thermoascus aurantiacus* CGMCC No. 0670.

In a specific preferred embodiment the protease is a variant of the metallo protease derived from *Thermoascus aurantiacus* disclosed as the mature part of SEQ ID NO. 2 disclosed in WO 2003/048353 or the mature part of SEQ ID NO: 1 in WO 2010/008841 or SEQ ID NO: 3 herein with mutations selected from the group of:

A27K+D79L+Y82F+S87G+D104P+A112P+A126V+D142L;

D79L+S87P+A112P+D142L; and

D79L+S87P+D142L.

In another preferred embodiment the protease is derived from a strain of *Pyrococcus furiosus*, such as the one shown in SEQ ID NO: 1 in U.S. Pat. No. 6,258,726 or SEQ ID NO: 13 herein.

In another embodiment the protease is one disclosed in SEQ ID NO: 13 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 13 herein. The *Pyroccus furiosus* protease can be purchased from Takara Shuzo Co. Ltd, Japan.

The *Pyrococcus furiosus* protease is a thermostable protease. The commercial product *Pyrococcus furiosus* protease (Pfu S) was found to have a thermostability of 110% (80° C./70° C.) and 103% (90° C./70° C.) at pH 4.5 determined as described in Example 2 herein.

It should be understood that these proteases are only examples. Any protease disclosed above in the "Protease Present and/or Added During Liquefaction" section above may be used as the protease component in a composition of the invention.

A composition of the invention may optionally further comprise a carbohydrate-source generating enzyme, in particular a glucoamylase, which has a heat stability at 85° C., pH 5.3, of at least 30%, preferably at least 35%.

In a preferred embodiment the carbohydrate-source generating enzyme is a glucoamylase having a relative activity of at least 80%, preferably at least 85%, preferably at least 90% at pH 4.5.

In a preferred embodiment carbohydrate-source generating enzyme is a glucoamylase having a pH stability at pH 4.5 of at least at least 80%, at least 85%, at least 90%, at least 95%, at least 100%.

Determination heat stability, and pH stability is described in the Example 4.

In a specific embodiment the carbohydrate-source generating enzyme is a glucoamylase, preferably derived from a strain of the genus *Penicillium*, especially a strain of *Penicillium oxalicum* disclosed in PCT/CN10/071753 published as WO 2011/127802. The glucoamylase may also be glucoamylase having at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802.

In a preferred embodiment the carbohydrate-source generating enzyme is a variant of the *Penicillium oxalicum* glucoamylase disclosed as SEQ ID NO: 2 in PCT/CN10/071753 published as WO 2011/127802 and shown in SEQ ID NO: 9 and 14 herein, having a K79V substitution (using the mature sequence shown in SEQ ID NO: 14 for numbering). The K79V glucoamylase variant has reduced sensitivity to protease degradation relative to the parent as disclosed in U.S. application No. 61/531,189 (which is hereby incorporated by reference).

A composition of the invention may further comprise a pullulanase. In a preferred embodiment the pullulanase includes an X47 domain as disclosed in U.S. 61/289,040 published as WO 2011/087836 (which are hereby incorporated by reference).

Specifically the pullulanase may be derived from a strain from the genus *Thermococcus*, including *Thermococcus litoralis* and *Thermococcus hydrothermalis* or a hybrid thereof.

The pullulanase may be *Thermococcus hydrothermalis* pullulanase truncated at site X4 or a *Thermococcus hydrothermalis/T. litoralis* hybrid enzyme with truncation site X4 as disclosed in U.S. 61/289,040 published as WO 2011/087836 or shown in SEQ ID NO: 12 herein.

In an embodiment the invention relates to a composition comprising:
i) an alpha-amylase having a T½ (min) at pH 4.5, 85° C., 0.12 mM CaCl$_2$) of at least 10 derived from *Bacillus stearothermophilus*;
ii) a protease having a thermostability value of more than 20% determined as Relative Activity at 80° C./70° C. derived from *Pyrococcus furiosus* or *Thermoascus aurantiacus*; and optionally
iii) a glucoamylase derived from *Penicillium oxalicum*.

The *Bacillus stearothermophilus* alpha-amylase, *Pyrococcus furiosus* or *Thermoascus aurantiacus* protease and/or *Penicillium oxalicum* glucoamylase may be any of the embodiment mentioned above.

In an embodiment the composition comprises a second alpha-amylase having a T % (min) at pH 4.5, 85° C., 0.12 mM CaCl$_2$) of less than 10 derived from *Bacillus stearothermophilus*.

In an embodiment the ratio of enzyme protein (weight basis) between the components in a composition of the invention may be:
Alpha-Amylase:Glucoamylase:Protease: 0.1-10:0.5-50:0.1-7, such as 0.5-3: 1-30:0.5-2, such as 1-2: 5-20:0.5-2.

Use of a Composition of the Invention

In a final aspect the invention relates to the use of a composition of the invention in a liquefaction process. In an embodiment liquefaction is a step in a process of the invention.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods

Materials:

Alpha-Amylase A: *Bacillus stearothermophilus* alpha-amylase with the mutations I181*+G182*+N193F truncated to 491 amino acids (SEQ ID NO: 1)

Alpha-Amylase 1093: *Bacillus stearothermophilus* alpha-amylase with the mutations I181*+G182*+N193F+E129V+K177L+R179E truncated to 491 amino acids (SEQ ID NO: 1)

Alpha-Amylase 1407: *Bacillus stearothermophilus* alpha-amylase with the mutations I181*+G182*+N193F+V59A+Q89R+E129V+K177L+R179E+H208Y+K220P+N224L+Q254S truncated to 491 amino acids (SEQ ID NO: 1)

Alpha-Amylase 1236: *Bacillus stearothermophilus* alpha-amylase with the mutations I181*+G182*+N193F+E129V+K177L+R179E+K220P+N224L+S242Q+Q254S truncated to 491 amino acids (SEQ ID NO: 1)

Protease 136: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: D79L+Y82F+S87P+A112P+A126V+D142L Protease 196: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: A27K+D79L+Y82F+S87G+D104P+A112P+A126V+D142L.

Protease 077: Metallo protease derived from *Thermoascus aurantiacus* CGMCC No. 0670 disclosed as amino acids 1-177 in SEQ ID NO: 3 herein and amino acids 1-177 in SEQ ID NO: 2 in WO 2003/048353 with the following mutations: A27K+D79L+S87P+A112P+D142L.

Protease Pfu: Protease derived from *Pyrococcus furiosus* purchased from Takara Bio Inc. (Japan) as Pfu Protease S (activity 10.5 mg/mL) and also shown in SEQ ID NO: 13 herein.

Glucoamylase PO: Mature part of the *Penicillium oxalicum* glucoamylase disclosed as SEQ ID NO: 2 in PCT/CN10/071753 published as WO 2011/127802 and shown in SEQ ID NO: 9 and 14 herein.

Glucoamylase PE001: Variant of the *Penicillium oxalicum* glucoamylase having a K79V substitution using the mature sequence shown in SEQ ID NO: 14 for numbering.

Glucoamylase BL: Blend of *Tamaromyces emersonii* glucoamylase disclosed in WO 99/28448 as SEQ ID NO: 7 and *Trametes cingulata* glucoamylase disclosed in WO 06/069289 in a ratio of about 9:1.

Glucoamylase BL2: Blend comprising *Talaromyces emersonii* glucoamylase disclosed in WO 99/28448, *Trametes cingulata* glucoamylase disclosed in WO 06/69289, and *Rhizomucor pusillus* alpha-amylase with *Aspergillus niger*-glucoamylase linker and SBD disclosed as V039 in Table 5 in WO 2006/069290 as side activities (ratio about 65:15:1)

Substrate in Example 9: Ground corn from Corn LP, Iowa, USA (84.19% DS) and backset (6.27% DS).

Pullulanase TH: Pullulanase from *Thermococcus hydrothermalis* shown in SEQ ID NO: 11 herein.

Yeast: RED STAR ETHANOL RED™ available from Red Star/Lesaffre, USA.

Methods

Identity: The relatedness between two amino acid sequences or between two nucleotide sequences is described by the parameter "identity".

For purposes of the present invention the degree of identity between two amino acid sequences, as well as the degree of identity between two nucleotide sequences, may be determined by the program "align" which is a Needleman-Wunsch alignment (i.e. a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotides.

"Align" is part of the FASTA package version v20u6 (see Pearson and Lipman, 1988, "Improved Tools for Biological Sequence Analysis", PNAS 85:2444-2448, and Pearson, 1990, "Rapid and Sensitive Sequence Comparison with FASTP and FASTA," *Methods in Enzymology* 183:63-98). FASTA protein alignments use the Smith-Waterman algorithm with no limitation on gap size (see "Smith-Waterman algorithm", Smith and Waterman, 1981, *J. Mol. Biol.* 147: 195-197).

Protease Assays

AZCL-Casein Assay

A solution of 0.2% of the blue substrate AZCL-casein is suspended in Borax/NaH$_2$PO$_4$ buffer pH9 while stirring. The solution is distributed while stirring to microtiter plate (100 microL to each well), 30 microL enzyme sample is added and the plates are incubated in an Eppendorf Thermomixer for 30 minutes at 45° C. and 600 rpm. Denatured enzyme sample (100° C. boiling for 20 min) is used as a blank. After incubation the reaction is stopped by transferring the microtiter plate onto ice and the coloured solution is separated from the solid by centrifugation at 3000 rpm for 5 minutes at 4° C. 60 microL of supernatant is transferred to a microtiter plate and the absorbance at 595 nm is measured using a BioRad Microplate Reader.

pNA-Assay 50 microL protease-containing sample is added to a microtiter plate and the assay is started by adding 100 microL 1 mM pNA substrate (5 mg dissolved in 100 microL DMSO and further diluted to 10 mL with Borax/NaH$_2$PO$_4$ buffer pH 9.0). The increase in OD$_{405}$ at room temperature is monitored as a measure of the protease activity.

Glucoamylase Activity (AGU)

Glucoamylase activity may be measured in Glucoamylase Units (AGU).

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
| --- | --- |
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
| --- | --- |
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

A folder (EB-SM-0131.02/01) describing this analytical method in more detail is available on request from Novozymes A/S, Denmark, which folder is hereby included by reference.

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M Ca$^{2+}$; and pH 5.6) dextrinizes 5260 mg starch dry substance Merck Amylum solubile.

A folder EB-SM-0009.02/01 describing this analytical method in more detail is available upon request to Novozymes A/S, Denmark, which folder is hereby included by reference.

Determination of Pullulanase Activity (NPUN)

Endo-pullulanase activity in NPUN is measured relative to a Novozymes pullulanase standard. One pullulanase unit (NPUN) is defined as the amount of enzyme that releases 1 micro mol glucose per minute under the standard conditions (0.7% red pullulan (Megazyme), pH 5, 40° C., 20 minutes). The activity is measured in NPUN/ml using red pullulan.

1 mL diluted sample or standard is incubated at 40° C. for 2 minutes. 0.5 mL 2% red pullulan, 0.5 M KCl, 50 mM citric acid, pH 5 are added and mixed. The tubes are incubated at 40° C. for 20 minutes and stopped by adding 2.5 ml 80% ethanol. The tubes are left standing at room temperature for 10-60 minutes followed by centrifugation 10 minutes at 4000 rpm. OD of the supernatants is then measured at 510 nm and the activity calculated using a standard curve.

The present invention is described in further detail in the following examples which are offered to illustrate the present invention, but not in any way intended to limit the scope of the invention as claimed. All references cited herein are specifically incorporated by reference for that which is described therein.

EXAMPLES

Example 1

Stability of Alpha-Amylase Variants

The stability of a reference alpha-amylase (*Bacillus stearothermophilus* alpha-amylase with the mutations I181*+G182*+N193F truncated to 491 amino acids (SEQ ID NO: 1)) and alpha-amylase variants thereof was determined by incubating the reference alpha-amylase and variants at pH 4.5 and 5.5 and temperatures of 75° C. and 85° C. with 0.12 mM CaCl$_2$ followed by residual activity determination using the EnzChek® substrate (EnzChek® Ultra Amylase assay kit, E33651, Molecular Probes).

Purified enzyme samples were diluted to working concentrations of 0.5 and 1 or 5 and 10 ppm (micrograms/ml) in enzyme dilution buffer (10 mM acetate, 0.01% Triton X100, 0.12 mM CaCl$_2$, pH 5.0). Twenty microliters enzyme sample was transferred to 48-well PCR MTP and 180 microliters stability buffer (150 mM acetate, 150 mM MES, 0.01% Triton X100, 0.12 mM CaCl$_2$, pH 4.5 or 5.5) was added to each well and mixed. The assay was performed using two concentrations of enzyme in duplicates. Before incubation at 75° C. or 85° C., 20 microliters was withdrawn and stored on ice as control samples. Incubation was performed in a PCR machine at 75° C. and 85° C. After incubation samples were diluted to 15 ng/mL in residual activity buffer (100 mM Acetate, 0.01% Triton X100, 0.12 mM CaCl$_2$, pH 5.5) and 25 microliters diluted enzyme was transferred to black 384-MTP. Residual activity was determined using the EnzChek substrate by adding 25 microliters substrate solution (100 micrograms/ml) to each well. Fluorescence was determined every minute for 15 minutes using excitation filter at 485-P nm and emission filter at 555 nm (fluorescence reader is Polarstar, BMG). The residual activity was normalized to control samples for each setup.

Assuming logarithmic decay half life time (T½ (min)) was calculated using the equation: T½ (min)=T(min)*LN (0.5)/LN(% RA/100), where T is assay incubation time in minutes, and % RA is % residual activity determined in assay.

Using this assay setup the half life time was determined for the reference alpha-amylase and variant thereof as shown in Table 1.

TABLE 1

| Mutations | T½ (min) (pH 4.5, 75° C., 0.12 mM CaCl$_2$) | T½ (min) (pH 4.5, 85° C., 0.12 mM CaCl$_2$) | T½ (min) (pH 5.5, 85° C., 0.12 mM CaCl$_2$) |
|---|---|---|---|
| Reference Alpha-Amylase A | 21 | 4 | 111 |
| Reference Alpha-Amylase A with the substitution V59A | 32 | 6 | 301 |
| Reference Alpha-Amylase A with the substitution V59E | 28 | 5 | 230 |
| Reference Alpha-Amylase A with the substitution V59I | 28 | 5 | 210 |
| Reference Alpha-Amylase A with the substitution V59Q | 30 | 6 | 250 |
| Reference Alpha-Amylase A with the substitutions V59A + Q89R + G112D + E129V + K177L + R179E + K220P + N224L + Q254S | 149 | 22 | ND |
| Reference Alpha-Amylase A with the substitutions V59A + Q89R + E129V + K177L + R179E + H208Y + K220P + N224L + Q254S | >180 | 28 | ND |
| Reference Alpha-Amylase A with the substitutions V59A + Q89R + E129V + K177L + R179E + K220P + N224L + Q254S + D269E + D281N | 112 | 16 | ND |
| Reference Alpha-Amylase A with the substitutions V59A + Q89R + E129V + K177L + R179E + K220P + N224L + Q254S + I270L | 168 | 21 | ND |
| Reference Alpha-Amylase A with the substitutions V59A + Q89R + E129V + K177L + R179E + K220P + N224L + Q254S + H274K | >180 | 24 | ND |
| Reference Alpha-Amylase A with the substitutions V59A + Q89R + E129V + K177L + R179E + K220P + N224L + Q254S + Y276F | 91 | 15 | ND |
| Reference Alpha-Amylase A with the substitutions V59A + E129V + R157Y + K177L + R179E + K220P + N224L + S242Q + Q254S | 141 | 41 | ND |
| Reference Alpha-Amylase A with the substitutions V59A + E129V + K177L + R179E + H208Y + K220P + N224L + S242Q + Q254S | >180 | 62 | ND |
| Reference Alpha-Amylase A with the substitutions V59A + E129V + K177L + R179E + K220P + N224L + S242Q + Q254S | >180 | 49 | >480 |
| Reference Alpha-Amylase A with the substitutions V59A + E129V + K177L + R179E + K220P + N224L + S242Q + Q254S + H274K | >180 | 53 | ND |
| Reference Alpha-Amylase A with the substitutions V59A + E129V + K177L + R179E + K220P + N224L + S242Q + Q254S + Y276F | >180 | 57 | ND |
| Reference Alpha-Amylase A with the substitutions V59A + E129V + K177L + R179E + K220P + N224L + S242Q + Q254S + D281N | >180 | 37 | ND |
| Reference Alpha-Amylase A with the substitutions V59A + E129V + K177L + R179E + K220P + N224L + S242Q + Q254S + M284T | >180 | 51 | ND |
| Reference Alpha-Amylase A with the substitutions V59A + E129V + K177L + R179E + K220P + N224L + S242Q + Q254S + G416V | >180 | 45 | ND |
| Reference Alpha-Amylase A with the substitutions V59A + E129V + K177L + R179E + K220P + N224L + Q254S | 143 | 21 | >480 |
| Reference Alpha-Amylase A with the substitutions V59A + E129V + K177L + R179E + K220P + N224L + Q254S + M284T | >180 | 22 | ND |
| Reference Alpha-Amylase A with the substitutions A91L + M96I + E129V + K177L + R179E + K220P + N224L + S242Q + Q254S | >180 | 38 | ND |
| Reference Alpha-Amylase A with the substitutions E129V + K177L + R179E | 57 | 11 | 402 |
| Reference Alpha-Amylase A with the substitutions E129V + K177L + R179E + K220P + N224L + S242Q + Q254S | 174 | 44 | >480 |
| Reference Alpha-Amylase A with the substitutions E129V + K177L + R179E + K220P + N224L + S242Q + Q254S + Y276F + L427M | >180 | 49 | >480 |
| Reference Alpha-Amylase A with the substitutions E129V + K177L + R179E + K220P + N224L + S242Q + Q254S + M284T | >180 | 49 | >480 |
| Reference Alpha-Amylase A with the substitutions E129V + K177L + R179E + K220P + N224L + S242Q + Q254S + N376* + I377* | 177 | 36 | >480 |
| Reference Alpha-Amylase A with the substitutions E129V + K177L + R179E + K220P + N224L + Q254S | 94 | 13 | >480 |
| Reference Alpha-Amylase A with the substitutions E129V + K177L + R179E + K220P + N224L + Q254S + M284T | 129 | 24 | >480 |
| Reference Alpha-Amylase A with the substitutions E129V + K177L + R179E + S242Q | 148 | 30 | >480 |
| Reference Alpha-Amylase A with the substitutions E129V + K177L + R179V | 78 | 9 | >480 |
| Reference Alpha-Amylase A with the substitutions E129V + K177L + R179V + K220P + N224L + S242Q + Q254S | 178 | 31 | >480 |
| Reference Alpha-Amylase A with the substitutions K220P + N224L + S242Q + Q254S | 66 | 17 | >480 |
| Reference Alpha-Amylase A with the substitutions K220P + N224L + Q254S | 30 | 6 | 159 |
| Reference Alpha-Amylase A with the substitution M284T | 35 | 7 | 278 |
| Reference Alpha-Amylase A with the substitutions M284V | 59 | 13 | ND |

ND not determined

ND not Determined

The results demonstrate that the alpha-amylase variants have a significantly greater half-life and stability than the reference alpha-amylase.

Example 2

Preparation of Protease Variants and Test of Thermostability

Chemicals used were commercial products of at least reagent grade.

Strains and Plasmids:

E. coli DH12S (available from Gibco BRL) was used for yeast plasmid rescue. pJTP000 is a S. cerevisiae and E. coli shuttle vector under the control of TPI promoter, constructed from pJC039 described in WO 01/92502, in which the Thermoascus aurantiacus M35 protease gene (WO 03/048353) has been inserted.

Saccharomyces cerevisiae YNG318 competent cells: MATa Dpep4[cir+] ura3-52, leu2-D2, his 4-539 was used for protease variants expression. It is described in J. Biol. Chem. 272(15): 9720-9727 (1997).

Media and Substrates

10×Basal solution: Yeast nitrogen base w/o amino acids (DIFCO) 66.8 g/L, succinate 100 g/l, NaOH 60 g/l.

SC-glucose: 20% glucose (i.e., a final concentration of 2%=2 g/100 mL)) 100 mL/L, 5% threonine 4 mL/L, 1% tryptophan10 ml/l, 20% casamino acids 25 ml/l, 10×basal solution 100 ml/l. The solution is sterilized using a filter of a pore size of 0.20 micrometer. Agar (2%) and H$_2$O (approx. 761 mL) is autoclaved together, and the separately sterilized SC-glucose solution is added to the agar solution.

YPD: Bacto peptone 20 g/l, yeast extract 10 g/L, 20% glucose 100 mL/L.

YPD+Zn: YPD+0.25 mM ZnSO$_4$.

PEG/LiAc solution: 40% PEG4000 50 ml, 5 M Lithium Acetate 1 mL.

96 well Zein micro titre plate:

Each well contains 200 microL of 0.05-0.1% of zein (Sigma), 0.25 mM ZnSO$_4$ and 1% of agar in 20 mM sodium acetate buffer, pH 4.5.

DNA Manipulations

Unless otherwise stated, DNA manipulations and transformations were performed using standard methods of molecular biology as described in Sambrook et al. (1989) Molecular cloning: A laboratory manual, Cold Spring Harbor lab. Cold Spring Harbor, NY; Ausubel, F. M. et al. (eds.) "*Current protocols in Molecular Biology*", John Wiley and Sons, 1995; Harwood, C. R. and Cutting, S. M. (Eds.).

Yeast Transformation

Yeast transformation was performed using the lithium acetate method. 0.5 microL of vector (digested by restriction endnucleases) and 1 microL of PCR fragments is mixed. The DNA mixture, 100 microL of YNG318 competent cells, and 10 microL of YEAST MAKER carrier DNA (Clontech) is added to a 12 mL polypropylene tube (Falcon 2059). Add 0.6 mL PEG/LiAc solution and mix gently. Incubate for 30 min at 30° C., and 200 rpm followed by 30 min at 42° C. (heat shock). Transfer to an eppendorf tube and centrifuge for 5 sec. Remove the supernatant and resolve in 3 mL of YPD. Incubate the cell suspension for 45 min at 200 rpm at 30° C. Pour the suspension to SC-glucose plates and incubate 30° C. for 3 days to grow colonies. Yeast total DNA are extracted by Zymoprep Yeast Plasmid Miniprep Kit (ZYMO research).

DNA Sequencing

E. coli transformation for DNA sequencing was carried out by electroporation (BIO-RAD Gene Pulser). DNA Plasmids were prepared by alkaline method (Molecular Cloning, Cold Spring Harbor) or with the Qiagen® Plasmid Kit. DNA fragments were recovered from agarose gel by the Qiagen gel extraction Kit. PCR was performed using a PTC-200 DNA Engine. The ABI PRISM™ 310 Genetic Analyzer was used for determination of all DNA sequences.

Construction of Protease Expression Vector

The Themoascus M35 protease gene was amplified with the primer pair Prot F (SEQ ID NO: 4) and Prot R (SEQ ID NO: 5). The resulting PCR fragments were introduced into S. cerevisiae YNG318 together with the pJC039 vector (described in WO 2001/92502) digested with restriction enzymes to remove the Humicola insolens cutinase gene.

The Plasmid in yeast clones on SC-glucose plates was recovered to confirm the internal sequence and termed as pJTP001.

Construction of Yeast Library and Site-Directed Variants

Library in yeast and site-directed variants were constructed by SOE PCR method (Splicing by Overlap Extension, see "PCR: A practical approach", p. 207-209, Oxford University press, eds. McPherson, Quirke, Taylor), followed by yeast in vivo recombination.

General Primers for Amplification and Sequencing

The primers AM34 (SEQ ID NO: 6) and AM35 (SEQ ID NO:7) were used to make DNA fragments containing any mutated fragments by the SOE method together with degenerated primers (AM34+Reverse primer and AM35+forward primer) or just to amplify a whole protease gene (AM34+AM35).

| PCR reaction system: | Conditions: |
|---|---|
| 48.5 microL H$_2$O | 1 94° C. 2 min |
| 2 beads puRe Taq Ready-To-Go PCR (Amersham Biosciences) | 2 94° C. 30 sec |
| 0.5 microL X 2 100 pmole/microL of primers | 3 55° C. 30 sec |
| 0.5 microL template DNA | 4 72° C. 90 sec |
| | 2-4 25 cycles |
| | 5 72° C. 10 min |

DNA fragments were recovered from agarose gel by the Qiagen gel extraction Kit. The resulting purified fragments were mixed with the vector digest. The mixed solution was introduced into Saccharomyces cerevisiae to construct libraries or site-directed variants by in vivo recombination.

Relative Activity Assay

Yeast clones on SC-glucose were inoculated to a well of a 96-well micro titre plate containing YPD+Zn medium and cultivated at 28° C. for 3 days. The culture supernatants were applied to a 96-well zein micro titer plate and incubated at at least 2 temperatures (ex., 70° C. and 80° C.) for more than 4 hours or overnight. The turbidity of zein in the plate was measured as A630 and the relative activity (higher/lower temperatures) was determined as an indicator of thermoactivity improvement. The clones with higher relative activity than the parental variant were selected and the sequence was determined.

Remaining Activity Assay

Yeast clones on SC-glucose were inoculated to a well of a 96-well micro titre plate and cultivated at 28° C. for 3 days. Protease activity was measured at 65° C. using azo-casein (Megazyme) after incubating the culture supernatant in 20 mM sodium acetate buffer, pH 4.5, for 10 min at a certain temperature (80° C. or 84° C. with 4° C. as a reference) to determine the remaining activity. The clones with higher remaining activity than the parental variant were selected and the sequence was determined.

Azo-Casein Assay 20 microL of samples were mixed with 150 microL of substrate solution (4 mL of 12.5% azo-casein in ethanol in 96 mL of 20 mM sodium acetate, pH 4.5, containing 0.01% triton-100 and 0.25 mM ZnSO$_4$) and incubated for 4 hours or longer.

After adding 20 microL/well of 100% trichloroacetic acid (TCA) solution, the plate was centrifuge and 100 microL of supernatants were pipette out to measure A440.

Expression of Protease Variants in *Aspergillus oryzae*

The constructs comprising the protease variant genes were used to construct expression vectors for *Aspergillus*. The *Aspergillus* expression vectors consist of an expression cassette based on the *Aspergillus niger* neutral amylase II promoter fused to the *Aspergillus nidulans* triose phosphate isomerase non translated leader sequence (Pna2/tpi) and the *Aspergillus niger* amyloglycosidase terminator (Tamg). Also present on the plasmid was the *Aspergillus* selective marker amdS from *Aspergillus nidulans* enabling growth on acetamide as sole nitrogen source. The expression plasmids for protease variants were transformed into *Aspergillus* as described in Lassen et al., 2001, *Appl. Environ. Microbiol.* 67: 4701-4707. For each of the constructs 10-20 strains were isolated, purified and cultivated in shake flasks.

Purification of Expressed Variants

1. Adjust pH of the 0.22 µm filtered fermentation sample to 4.0.
2. Put the sample on an ice bath with magnetic stirring. Add (NH$_4$)$_2$SO$_4$ in small aliquots (corresponding to approx. 2.0-2.2 M (NH$_4$)$_2$SO$_4$ not taking the volume increase into account when adding the compound).
3. After the final addition of (NH$_4$)$_2$SO$_4$, incubate the sample on the ice bath with gentle magnetic stirring for min. 45 min.
4. Centrifugation: Hitachi himac CR20G High-Speed Refrigerated Centrifuge equipped with R20A2 rotor head, 5° C., 20,000 rpm, 30 min.
5. Dissolve the formed precipitate in 200 mL 50 mM Na-acetate pH 4.0.
6. Filter the sample by vacuum suction using a 0.22 micro m PES PLUS membrane (IWAKI).
7. Desalt/buffer-exchange the sample to 50 mM Na-acetate pH 4.0 using ultrafiltration (Vivacell 250 from Vivascience equipped with 5 kDa MWCO PES membrane) overnight in a cold room. Dilute the retentate sample to 200 ml using 50 mM Na-acetate pH 4.0. The conductivity of sample is preferably less than 5 mS/cm.
8. Load the sample onto a cation-exchange column equilibrated with 50 mM Na-acetate pH 4.0. Wash unbound sample out of the column using 3 column volumes of binding buffer (50 mM Na-acetate pH 4.0), and elute the sample using a linear gradient, 0-100% elution buffer (50 mM Na-acetate+1 M NaCl pH 4.0) in 10 column volumes.
9. The collected fractions are assayed by an endo-protease assay (cf. below) followed by standard SDS-PAGE (reducing conditions) on selected fractions. Fractions are pooled based on the endo-protease assay and SDS-PAGE.

Endo-Protease Assay

1. Protazyme OL tablet/5 ml 250 mM Na-acetate pH 5.0 is dissolved by magnetic stirring (substrate: endo-protease Protazyme AK tablet from Megazyme—cat. #PRAK 11/08).
2. With stirring, 250 microL of substrate solution is transferred to a 1.5 mL Eppendorf tube.
3. 25 microL of sample is added to each tube (blank is sample buffer).
4. The tubes are incubated on a Thermomixer with shaking (1000 rpm) at 50° C. for 15 minutes.
5. 250 microL of 1 M NaOH is added to each tube, followed by vortexing.
6. Centrifugation for 3 min. at 16,100×G and 25° C.
7. 200 microL of the supernatant is transferred to a MTP, and the absorbance at 590 nm is recorded.

TABLE 2

Relative Activity of protease variants. Numbering of substitution(s) starts from N-terminal of the mature peptide in amino acids 1 to 177 of SEQ ID NO: 3.

| | | Remaining Activity | |
|---|---|---|---|
| Variant | Substitution(s) and/or deletion(s) | 80° C. | 84° C. |
| JTP082 | ΔS5/D79L/S87P/A112P/D142L | | 53% |
| JTP091 | D79L/S87P/A112P/T124V/D142L | 43% | |
| JTP092 | ΔS5/N26R/D79L/S87P/A112P/D142L | | 60% |
| JTP095 | N26R/T46R/D79L/S87P/A112P/D142L | | 62% |
| JTP096 | T46R/D79L/S87P/T116V/D142L | | 67% |
| JTP099 | D79L/P81R/S87P/A112P/D142L | | 80% |
| JTP101 | A27K/D79L/S87P/A112P/T124V/D142L | 81% | |
| JTP116 | D79L/Y82F/S87P/A112P/T124V/D142L | 59% | |
| JTP117 | D79L/Y82F/S87P/A112P/T124V/D142L | 94% | |
| JTP127 | D79L/S87P/A112P/T124V/A126V/D142L | 53% | |

TABLE 3

Relative Activity of protease variants. Numbering of substitution(s) starts from N-terminal of the mature peptide in amino acids 1 to 177 of SEQ ID NO: 3.

| | | Relative Activity | |
|---|---|---|---|
| Variant | Substitutions | 80° C./70° C. | 85° C./70° C. |
| JTP050 | D79L S87P A112P D142L | 23% | 9% |
| JTP134 | D79L Y82F S87P A112P D142L | 40% | |
| JTP135 | S38T D79L S87P A112P A126V D142L | 62% | |
| JTP136 | D79L Y82F S87P A112P A126V D142L | 59% | |
| JTP137 | A27K D79L S87P A112P A126V D142L | 54% | |
| JTP145 | S49P D79L S87P A112P D142L | 59% | |
| JTP146 | S50P D79L S87P A112P D142L | 63% | |
| JTP148 | D79L S87P D104P A112P D142L | 64% | |
| JTP161 | D79L Y82F S87G A112P D142L | 30% | 12% |
| JTP180 | S70V D79L Y82F S87G Y97W A112P D142L | 52% | |
| JTP181 | D79L Y82F S87G Y97W D104P A112P D142L | 45% | |
| JTP187 | S70V D79L Y82F S87G A112P D142L | 45% | |
| JTP188 | D79L Y82F S87G D104P A112P D142L | 43% | |
| JTP189 | D79L Y82F S87G A112P A126V D142L | 46% | |
| JTP193 | Y82F S87G S70V D79L D104P A112P D142L | | 15% |
| JTP194 | Y82F S87G D79L D104P A112P A126V D142L | | 22% |
| JTP196 | A27K D79L Y82F S87G D104P A112P A126V D142L | | 18% |

TABLE 4

Relative Activity of protease variants. Numbering of substitution(s) starts from N-terminal of the mature peptide in amino acids 1 to 177 of SEQ ID NO: 3.

| Variant | Substitutions | Relative Activity 80° C./70° C. |
|---|---|---|
| JTP196 | A27K D79L Y82F S87G D104P A112P A126V D142L | 55% |
| JTP210 | A27K Y82F S87G D104P A112P A126V D142L | 36% |
| JTP211 | A27K D79L Y82F D104P A112P A126V D142L | 44% |
| JTP213 | A27K Y82F D104P A112P A126V D142L | 37% |

Example 3

Temperature Profile of Selected Protease Variants Using Purified Enzymes

Selected protease variants showing good thermostability were purified and the purified enzymes were used in a zein-BCA assay as described below. The remaining protease activity was determined at 60° C. after incubation of the enzyme at elevated temperatures as indicated for 60 min.

Zein-BCA Assay:

Zein-BCA assay was performed to detect soluble protein quantification released from zein by variant proteases at various temperatures.

Protocol:
1☐ Mix 10 microL of 10 micro g/mL enzyme solutions and 100 microL of 0.025% zein solution in a micro titer plate (MTP).
2☐ Incubate at various temperatures for 60 min.
3☐ Add 10 microL of 100% trichloroacetic acid (TCA) solution.
4☐ Centrifuge MTP at 3500 rpm for 5 m.
5☐ Take out 15 microL to a new MTP containing 100 microL of BOA assay solution (Pierce Cat #: 23225, BOA Protein Assay Kit).
6☐ Incubate for 30 min. at 60° C.
7☐ Measure A562.

The results are shown in Table 5. All of the tested protease variants showed an improved thermostability as compared to the wild type (WT) protease.

TABLE 5

Zein-BCA assay

Sample incubated 60 min at indicated temperatures (° C.)
(micro g/mL Bovine serum albumin equivalent peptide released)

| WT/Variant | 60° C. | 70° C. | 75° C. | 80° C. | 85° C. | 90° C. | 95° C. |
|---|---|---|---|---|---|---|---|
| WT | 94 | 103 | 107 | 93 | 58 | 38 | |
| JTP050 (D79L + S87P + A112P + D142L) | 86 | 101 | 107 | 107 | 104 | 63 | 36 |
| JTP077 (A27K + D79L + S87P + A112P + D142L) | 82 | 94 | 104 | 105 | 99 | 56 | 31 |
| JTP188 (D79L + Y82F + S87G + D104P + A112P + D142L) | 71 | 83 | 86 | 93 | 100 | 75 | 53 |
| JTP196 (A27K + D79L + Y82F + S87G + D104P + A112P + A126V + D142L) | 87 | 99 | 103 | 106 | 117 | 90 | 38 |

Example 4

Characterization of *Penicillium oxalicum* Glucoamylase

The *Penicillium oxalicum* glucoamylase is disclosed WO 2011/127802 and in SEQ ID NO: 9 herein.

Substrate. Substrate: 1% soluble starch (Sigma S-9765) in deionized water

Reaction buffer: 0.1 M Acetate buffer at pH 5.3

Glucose concentration determination kit: Wako glucose assay kit (LabAssay glucose, WAKO, Cat #298-65701).

Reaction condition. 20 microL soluble starch and 50 microL acetate buffer at pH5.3 were mixed. 30 microL enzyme solution (50 micro g enzyme protein/ml) was added to a final volume of 100 microL followed by incubation at 37° C. for 15 min.

The glucose concentration was determined by Wako kits.

All the work carried out in parallel.

Temperature optimum. To assess the temperature optimum of the *Penicillium oxalicum* glucoamylase the "Reaction condition"-assay described above was performed at 20, 30, 40, 50, 60, 70, 80, 85, 90 and 95° C. The results are shown in Table 6.

TABLE 6

| | Temperature optimum |||||||||| 
|---|---|---|---|---|---|---|---|---|---|---|
| | Temperature (° C.) |||||||||| 
| | 20 | 30 | 40 | 50 | 60 | 70 | 80 | 85 | 90 | 95 |
| Relative activity (%) | 63.6 | 71.7 | 86.4 | 99.4 | 94.6 | 100.0 | 92.9 | 92.5 | 82.7 | 82.8 |

From the results it can be seen that the optimal temperature for *Penicillium oxalicum* glucoamylase at the given conditions is between 50° C. and 70° C. and the glucoamylase maintains more than 80% activity at 95° C.

Heat stability. To assess the heat stability of the *Penicillium oxalicum* glucoamylase the Reaction condition assay was modified in that the enzyme solution and acetate buffer was preincubated for 15 min at 20, 30, 40, 50, 60, 70, 75, 80, 85, 90 and 95° C. Following the incubation 20 microL of starch was added to the solution and the assay was performed as described above.

The results are shown in Table 7.

TABLE 7

| | Heat stability |||||||||| 
|---|---|---|---|---|---|---|---|---|---|---|
| | Temperature (° C.) |||||||||| 
| | 20 | 30 | 40 | 50 | 60 | 70 | 80 | 85 | 90 | 95 |
| Relative activity (%) | 91.0 | 92.9 | 88.1 | 100.0 | 96.9 | 86.0 | 34.8 | 36.0 | 34.2 | 34.8 |

From the results it can be seen that *Penicillium oxalicum* glucoamylase is stable up to 70° C. after preincubation for 15 min in that it maintains more than 80% activity.

pH optimum. To assess the pH optimum of the *Penicillium oxalicum* glucoamylase the Reaction condition assay described above was performed at pH 2.0, 3.0, 3.5, 4.0, 4.5, 5.0, 6.0 7.0, 8.0, 9.0, 10.0 and 11.0. Instead of using the acetate buffer described in the Reaction condition assay the following buffer was used 100 mM Succinic acid, HEPES, CHES, CAPSO, 1 mM $CaCl_2$, 150 mM KCl, 0.01% Triton X-100, pH adjusted to 2.0, 3.0, 3.5, 4.0, 4.5, 5.0, 6.0 7.0, 8.0, 9.0, 10.0 or 11.0 with HCl or NaOH.

The results are shown in Table 8.

TABLE 8

| | pH optimum |||||||||||| 
|---|---|---|---|---|---|---|---|---|---|---|---|---|
| | pH |||||||||||| 
| | 2.0 | 3.0 | 3.5 | 4.0 | 4.5 | 5.0 | 6.0 | 7.0 | 8.0 | 9.0 | 10.0 | 11.0 |
| Relative activity (%) | 71.4 | 78.6 | 77.0 | 91.2 | 84.2 | 100.0 | 55.5 | 66.7 | 30.9 | 17.8 | 15.9 | 16.1 |

From the results it can be seen that *Penicillium oxalicum* glucoamylase at the given conditions has the highest activity at pH 5.0. The *Penicillium oxalicum* glucoamylase is active in a broad pH range in the it maintains more than 50% activity from pH 2 to 7.

pH stability. To assess the heat stability of the *Penicillium oxalicum* glucoamylase the Reaction condition assay was modified in that the enzyme solution (50 micro g/mL) was preincubated for 20 hours in buffers with pH 2.0, 3.0, 3.5, 4.0, 4.5, 5.0, 6.0 7.0, 8.0, 9.0, 10.0 and 11.0 using the buffers described under pH optimum. After preincubation, 20 microL soluble starch to a final volume of 100 microL was added to the solution and the assay was performed as described above.

The results are shown in Table 9.

TABLE 9

| | pH stability | | | | | | | | | | | |
|---|---|---|---|---|---|---|---|---|---|---|---|---|
| | pH | | | | | | | | | | | |
| | 2.0 | 3.0 | 3.5 | 4.0 | 4.5 | 5.0 | 6.0 | 7.0 | 8.0 | 9.0 | 10.0 | 11.0 |
| Relative activity (%) | 17.4 | 98.0 | 98.0 | 103.2 | 100.0 | 93.4 | 71.2 | 90.7 | 58.7 | 17.4 | 17.0 | 17.2 |

From the results it can be seen that *Penicillium oxalicum* glucoamylase, is stable from pH 3 to pH 7 after preincubation for 20 hours and it decreases its activity at pH 8.

Example 5

Improved Ethanol Production Process
Mash Preparation: Corn mashes were prepared through liquefaction in an 85° C. water bath for 2 hours. The dry solids (DS) content was around 30-33% and the backset ratio around 30%.
Mash Preparation: Corn slurries were prepared for liquefaction by weighing out the specified amounts of ground corn, backset, and tap water into Nalgene bottles. Slurries were pH-adjusted to either 5.80 (Control) using 50% w/w NaOH or 4.50 (Study A, B) or 4.80 (Study C, D, E, F) using 40% v/v $H_2SO_4$. Control mashes using Alpha-Amylase A were made at pH 5.8. Aliquots of enzyme stock solutions were added. Bottles were tightly capped and placed into the water bath. Slurries were shaken vigorously once every 5 minutes for the first 30 minutes and then once every 30 minutes thereafter for a total of 2 hours. Mashes were immediately cooled in an ice bath. Urea and penicillin were then added to each mash to reach concentrations of 500 and 3 ppm, respectively.
Fermentation Setup: Mashes were adjusted to pH 5.0 using 40% $H_2SO_4$ or 50% NaOH. Approximately 5 g of each mash was transferred into pre-weighed 15 mL plastic Falcon centrifuge tubes for fermentation. Typically, five replicate fermentations were prepared for each treatment. A small hole was drilled into the lid of each tube to allow for $CO_2$ release during fermentation. Following mash transfer, all tubes were reweighed to obtain their initial sample weights. Into each tube was then added 100 microL of rehydrated RED STAR ETHANOL RED yeast (rehydrated by weighing 5.5 g of dry yeast into a 150 mL Erlenmeyer flask, adding 100 mL of tap water and stirring in a 32° C. water bath for 30 minutes), an aliquot of diluted Glucoamylase BL (diluted in deionized water) needed to reach starting concentrations of 0.50 AGU/g DS. Deionized water was added to each tube such that the total volume of liquid added to each tube relative to the sample weight was the same. All tubes were then reweighed and then placed into a water bath set at 32° C. Fermentation was typically allowed to progress for 54 hours (if nothing else is stated). Tubes were vigorously vortexed after approximately 7 hours and then vortexed and reweighed twice per day for the remaining fermentation time. The grams of ethanol produced per gram of dry solids in each tube were calculated from the weight loss data according to the following equation:

$$g\ ethanol/g\ DS = \frac{g\ CO_2\ weight\ loss \times \frac{1\ mol\ CO_2}{44.0098\ g\ CO_2} \times \frac{1\ mol\ ethanol}{1\ mol\ CO_2} \times \frac{46.094\ g\ ethanol}{1\ mol\ ethanol}}{g\ corn\ in\ tube \times \%\ DS\ of\ Corn}$$

Typically, 4 replicate tubes for each treatment were pulled after 54 hours of fermentation for HPLC analysis. Pulled samples were treated with 50 microL of 40% $H_2SO_4$ to stop fermentation and vortexed thoroughly. The samples were then centrifuged at 1460×g for 10 minutes and then filtered into HPLC vials through 0.45 micro m syringe filters. HPLC analysis was finally conducted on the samples to quantify the amounts of ethanol.
Results
An overview of the results is provided in Table 10.

TABLE 10

The doses of enzymes are listed in parentheses for each and are expressed as micro g EP/g DS.

| Study | pH | Enzymes In liquefaction step i). | Glucoamylase In SSF | HPLC EtOH vs Reference Alpha-Amylase A (Control) |
|---|---|---|---|---|
| A | 4.5 | Alpha-Amylase 1093 (1.4) Protease 077 (2) Pullulanase TH (2) | Glucoamylase BL | 3.0% |
| B | 4.5 | Alpha-amylase 1093 (2.75) Protease 077 (5) Pullulanase TH (2) | Glucoamylase BL | 1.6% |
| C | 4.8 | Alpha-amylase 1236 (2) Protease 136 (2) Glucoamylase PO (15) | Glucoamylase BL | 4.7% |
| D | 4.8 | Alpha-Amylase 1093 (2) Protease 180 (2.1) Glucoamylase PO (10) | Glucoamylase BL | 4.2% (48 hrs) |
| E | 4.8 | Alpha-Amylase 1236 (2) Protease 188 (2) Glucoamylase PO (15) | Glucoamylase BL | 7.1% |
| F | 4.8 | Alpha-Amylase 1407 (1) Protease 196 (2) Glucoamylase PO (2) | Glucoamylase BL | 4.8% (at 72 hrs) |

*measured at 54 hours unless otherwise noted.

Example 6

Whole Corn Liquefaction and SSF Process Using the *P. Oxalicum* AMG Variant (PE001)
The *Penicillium oxalicum* glucoamylase (Glucoamylase PO) variant, Glucoamylase PE001, showing reduced sensitivity to protease degradation, was tested in both whole corn liquefaction and starch saccharification (shown in next section). For the whole corn liquefactions, the Glucoamylase PE001 enzyme was added in different doses with a low pH amylase variant, Alpha-Amylase 1407. In some liquefactions, the Glucoamylase PE001 variant was tested with both the low pH amylase Alpha-Amylase 1407 and the thermostable protease Protease 196. In all experiments, the liquefactions were done using the automated system called the "Lab-O-Mat". This instrument controls the temperature and provides constant mixing. The other experimental conditions were: pH was 4.8 (for the liquefacts containing the Alpha-Amylase 1407 low pH amylase) or 5.8 (for the Alpha-Amylase A control), 32% dry solids, 85° C., 2 hours total time. The enzyme dosing schemes are shown in Table 11. The liquefied mashes were saccharified and fermented using Glucoamylase BL2 (at a dose of 0.5 AGU/gram dry solids for 54 hours at 32° (C).

TABLE 11

Enzyme dosing scheme for the three whole corn liquefaction experiments done using Glucoamylase PO protease nicking stable variant, i.e., Glucoamylase PE001.

| Alpha-Amylase (Dose) | Protease (Dose) | Glucoamylase (Dose) |
|---|---|---|
| Alpha-Amylase A (0.02% w/w corn) | None | None |
| Alpha-Amylase 1407 (1.4 µg EP/g DS) | None | None |
| Alpha-Amylase 1407 (1.4 µg EP/g DS) | None | Glucoamylase PO (P3HK) (10 µg EP/g DS) |
| Alpha-Alpha 1407 (1.4 µg EP/g DS) | None | Glucoamylase PE001 (10 µg EP/g DS) |
| Alpha-Amylase 1407 (1.4 µg EP/g DS) | Protease 196 (1 µg EP/g DS) | Glucoamylase PO (P3HK) (10 µg EP/g DS) |
| Alpha-Amylase 1407 (1.4 µg EP/g DS) | Protease 196 (1 µg EP/g DS) | Glucoamylase PE001 (10 µg EP/g DS) |

The HPLC quantified ethanol titers (in grams per liter) are shown in Table 12.

TABLE 12

Average ethanol titers and associated standard deviations, in grams per liter. The Protease196 is a temperature stable protease described in WO 2011/072191 and Alpha-Amylase 1407 is a low pH amylase described in WO 2011/082425.

| Treatment | Ethanol (Average ± Standard deviation; grams/liter) |
|---|---|
| Alpha-Amylase A control | 126.4 ± 0.3 |
| Alpha-Amylase 1407 (low pH alpha-amylase variant) control | 126.7 ± 0.3 |
| Glucoamylase PO (wild-type) P3HK (10 µg EP/g DS) | 127.2 ± 0.4 |
| Glucoamylase PE001 variant (10 µg EP/g DS) | 127.1 ± 0.5 |
| Glucoamylase PO (wild-type) P3HK (10 µg EP/g DS) + Protease 196 (1 µg EP/g DS) | 127.6 ± 0.4 |
| Glucoamylase PE001 variant (10 µg EP/g DS) + Protease 196 (1 µg EP/g DS) | 127.7 ± 0.2 |

Example 7

Thermostability of Protease Pfu

The thermostability of the *Pyrococcus furiosus* protease (Pfu S) purchased from Takara Bio, (Japan) was tested using the same methods as in Example 2. It was found that the thermostability (Relative Activity) was 110% at (80° C./70° C.) and 103% (90° C./70° C.) at pH 4.5.

Example 8

Ethanol Production Using Alpha-Amylase 1407 and Pfu Protease for Liquefaction

The purpose of this experiment was to evaluate application performance of Protease Pfu derived from *Pyrococcus furiosus* at pH 4.8 during liquefaction at 85° C. for 2 hours. Liquefaction (Labomat)

Each liquefaction received ground corn (84.19% DS), backset (6.27% DS), and tap water targeting a total weight of 100 g at 32.50% Dry Solids (DS). Backset was blended at 30% w/w of total slurry weight. Initial slurry pH was approximately 5.2 and was adjusted to pH 4.8 with 40% v/v sulfuric acid prior to liquefaction. All enzymes were added according to the experimental design listed in Table 13 below. Liquefaction took place in a Labomat using the following conditions: 5° C./min. Ramp, 17 minute Ramp, 103 minute hold time, 40 rpm for the entire run, 200 mL stainless steel canisters. After liquefaction, all canisters were cooled in an ice bath and prepared for fermentation based on the protocol listed below under SSF.

Simultaneous Saccharification and Fermentation (SSF)

Each mash was adjusted to pH 5.0 with 50% w/w Sodium Hydroxide or 40% v/v sulfuric acid. Penicillin was applied to each mash to a total concentration of 3 ppm. The tubes were prepared with mash by aliquoting approximately 4.5 g of mash per 15 mL pre-drilled test tubes to allow $CO_2$ release. The test tubes sat, overnight, at 4° C. until the next morning.

All test tubes of mash were removed from cold storage and warmed up to 32° C. in the walk-in incubation chamber. Once warmed, Glucoamylase BL2, was dosed to each tube of mash at 0.50 AGU/g DS, water was added so that all tubes received 120 µL of liquid and each mash sample received 100 µL of rehydrated yeast. Rehydrated yeast was prepared by mixing 5.5 g of Fermentis RED STAR into 100 mL of 32° C. tap water for at least 15 minutes.

In monitoring $CO_2$ weight-loss over time, each unit of $CO_2$ generated and lost is converted to gram ethanol produced per gram of dry solids (g EtOH/gDS) by the following:

$$\text{g ethanol}/\text{g } DS = \frac{\text{g CO2 weight loss} \times \frac{1\text{mol CO2}}{44.0098 \text{ g CO2}} \times \frac{1\text{mol ethanol}}{1\text{mol CO2}} \times \frac{46.094 \text{ g ethanol}}{1\text{mol ethanol}}}{\text{g mash in tube } \% \ DS \text{ of mash}}$$

HPLC Analysis

Fermentation sampling took place after 54 hours of fermentation by taking 3 tubes per treatment. Each sample was deactivated with 50 µL of 40% v/v $H_2SO_4$, vortexing, centrifuging at 1460×g for 10 minutes, and filtering through a 0.45 µm Whatman PP filter. 54 hour samples were analyzed under HPLC without further dilution. Samples were stored at 4° C. prior to and during HPLC analysis.

| HPLC system | Agilent's 1100/1200 series with Chem station software Degasser, Quaternary Pump, Auto-Sampler, Column Compartment/w Heater Refractive Index Detector (RI) |
|---|---|
| Column | Bio-Rad HPX- 87H Ion Exclusion Column 300 mm × 7.8 mm part# 125-0140 Bio-Rad guard cartridge cation H part# 125-0129, Holder part# 125-0131 |
| Method | 0.005M $H_2SO_4$ mobile phase Flow rate: 0.6 ml/min Column temperature: 65° C. RI detector temperature: 55° C. |

The method quantified analyte(s) using calibration standard for ethanol (% w/v). A four point calibration including the origin is used for quantification.

Where applicable, data were analyzed using JMP software (Cary, NC) with Oneway ANOVA of pairs using Tukey- Kramer HSD or Dunnett's. Error bars denoting the 95% confidence level were established by multiplying the standard error of Oneway Anova analysis by 1.96.

TABLE 13

Experimental Plan.
Liquefaction at 85° C. (pH 4.8)

| Alpha-amylase | Dose µg/g DS | Protease | Dose µg/g DS | Glucoamylase | Dose µg/g DS |
|---|---|---|---|---|---|
| 1407 | 1.4 | — | — | — | — |
| 1407 | 1.4 | Pfu | 2 | — | — |
| 1407 | 1.4 | Pfu | 2 | PE001 | 10 |

Figure 1:
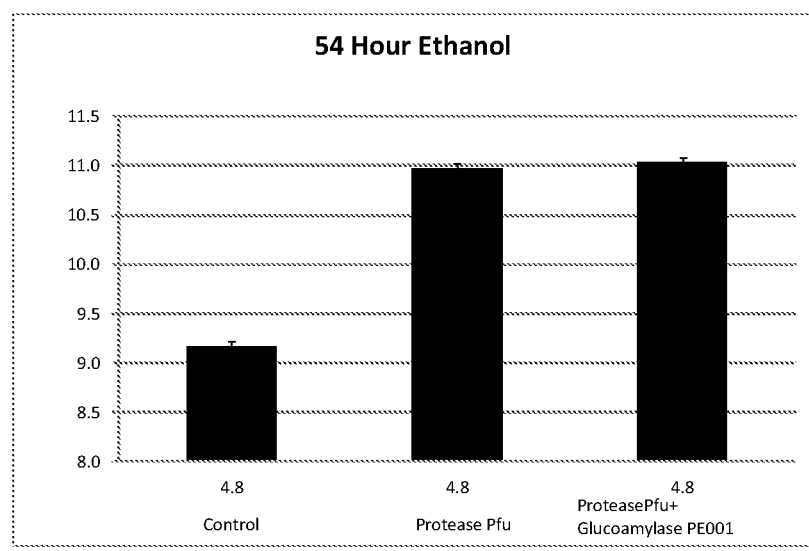
FIG. 1 shows a comparison of 54 hour ethanol for liquefactions (85° C.) prepared with Alpha-Amylase 1407 with and without Protease Pfu or Glucoamylase PE001 at pH 4.8.
Figure 2:
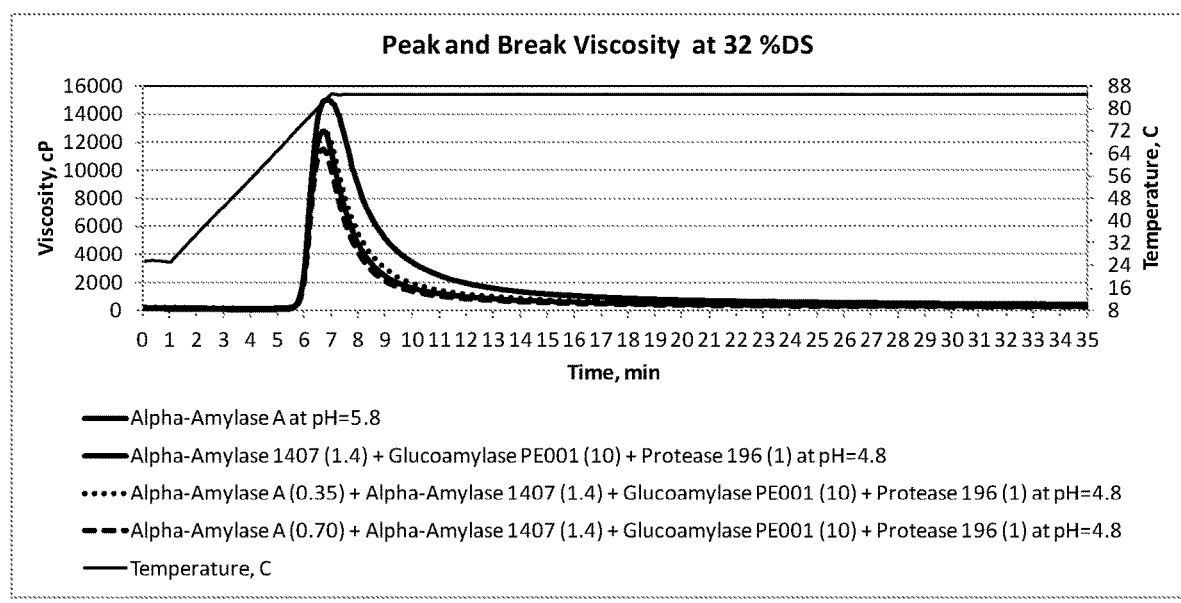
FIG. 2 shows the peak and break viscosity at 32% DS for the experiment in Example 10 comparing
  Alpha-Amylase A (1.4 micro g) (pH 5.8);
  Alpha-Amylase 1407 (1.4 micro g)+Glucoamylase PE001 (10 micro g)+Protease 196 (1 micro g) (pH 4.8);
  Alpha-Amylase A (0.35 micro g)+Alpha-Amylase 1407 (1.4 micro g)+Glucoamylase PE001 (10 micro g)+Protease 196 (1 micro g) (pH 4.8);
  Alpha-Amylase A (0.7 micro g)+Alpha-Amylase 1407 (1.4 micro g)+Glucoamylase PE001 (10 micro g)+Protease 196 (1 micro g) (pH 4.8)
Figure 3:
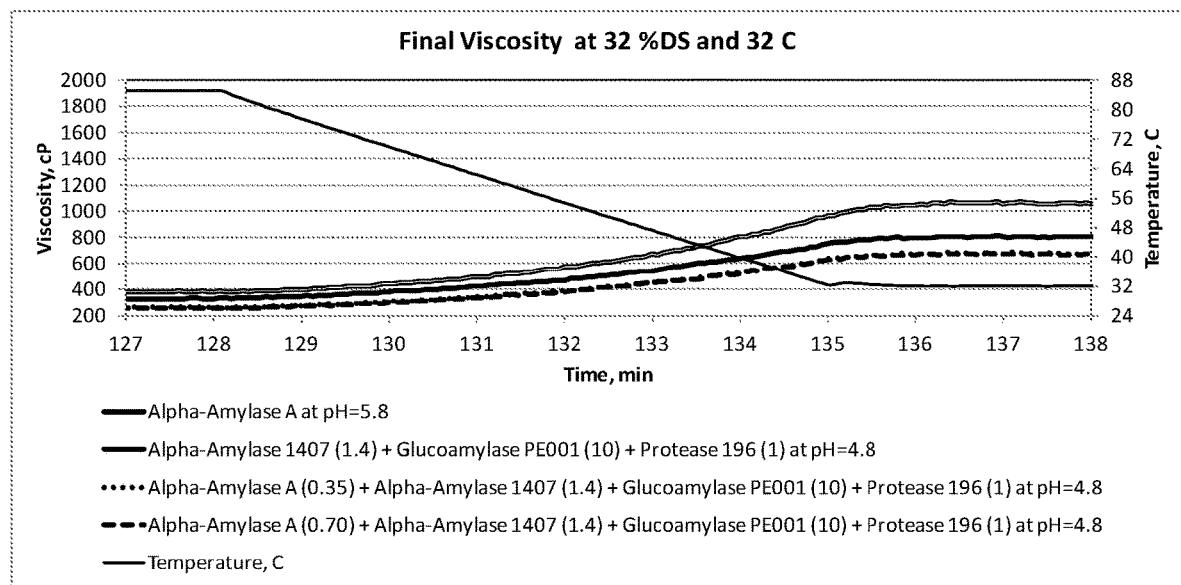
FIG. 3 shows the final viscosity at 32% DS at 32° C. for the experiment in Example 10 comparing
  Alpha-Amylase A (1.4 micro g) (pH 5.8);
  Alpha-Amylase 1407 (1.4 micro g)+Glucoamylase PE001 (10 micro g)+Protease 196 (1 micro g) (pH 4.8)

Table 14 and FIG. 1 below show the results:

TABLE 14 and FIG. 1 below shows the results:

| Treatment | pH | EtOH (% w/v) | EtOH (% Δ) | JMP Std Error | 95% CI |
|---|---|---|---|---|---|
| Control | 4.8 | 9.2 | 100% | 0.022 | 0.042 |
| Pfu | 4.8 | 11.0 | 120% | 0.022 | 0.042 |
| Pfu + PE001 | 4.8 | 11.0 | 120% | 0.022 | 0.042 |

Example 9

Ethanol Production Using Alpha-Amylase 1407 and Pfu Protease for Liquefaction

The purpose of this experiment was to evaluate application performance of Protease Pfu derived from *Pyrococcus furiosus* at pH 4.8 during liquefaction at 85° C. for 2 hours.

Liquefaction (Labomat)

Each liquefaction received ground corn (84.19% DS), backset (6.27% DS), and tap water targeting a total weight of 100 g at 32.50% Dry Solids (DS). Backset was blended at 30% w/w of total slurry weight. Initial slurry pH was approximately 5.2 and was adjusted to pH 4.8 with 40% v/v sulfuric acid prior to liquefaction. All enzymes were added according to the experimental design listed in Table 13 below. Liquefaction took place in a Labomat using the following conditions: 5° C./min. Ramp, 17 minute Ramp, 103 minute hold time, 40 rpm for the entire run, 200 mL stainless steel canisters. After liquefaction, all canisters were cooled in an ice bath and prepared for fermentation based on the protocol listed below under SSF.

Simultaneous Saccharification and Fermentation (SSF)

Each mash was adjusted to pH 5.0 with 50% w/w Sodium Hydroxide or 40% v/v sulfuric acid. Penicillin was applied to each mash to a total concentration of 3 ppm. The tubes were prepared with mash by aliquoting approximately 4.5 g of mash per 15 mL pre-drilled test tubes to allow $CO_2$ release. The test tubes sat, overnight, at 4° C. until the next morning.

All test tubes of mash were removed from cold storage and warmed up to 32° C. in the walk-in incubation chamber. Once warmed, Glucoamylase BL2, was dosed to each tube of mash at 0.50 AGU/g DS, water was added so that all tubes received 120 µL of liquid and each mash sample received 100 µL of rehydrated yeast. Rehydrated yeast was prepared by mixing 5.5 g of Fermentis RED STAR into 100 mL of 32° C. tap water for at least 15 minutes.

In monitoring $CO_2$ weight-loss over time, each unit of $CO_2$ generated and lost is converted to gram ethanol produced per gram of dry solids (g EtOH/gDS) by the following:

$$\text{g ethanol/g } DS = \frac{\text{g CO2 weight loss} \times \frac{1\text{mol CO2}}{44.0098 \text{ g CO2}} \times \frac{1\text{mol ethanol}}{1\text{mol CO2}} \times \frac{46.094 \text{ g ethanol}}{1\text{mol ethanol}}}{\text{g mash in tube} \times \% \, DS \text{ of mash}}$$

HPLC Analysis

Fermentation sampling took place after 54 hours of fermentation by taking 3 tubes per treatment. Each sample was deactivated with 50 µL of 40% v/v $H_2SO_4$, vortexing, centrifuging at 1460×g for 10 minutes, and filtering through a 0.45 µm Whatman PP filter. 54 hour samples were analyzed under HPLC without further dilution. Samples were stored at 4° C. prior to and during HPLC analysis.

| | |
|---|---|
| HPLC system | Agilent's 1100/1200 series with Chem station software Degasser, Quaternary Pump, Auto-Sampler, Column Compartment/w Heater Refractive Index Detector (RI) |
| Column | Bio-Rad HPX- 87H Ion Exclusion Column 300 mm × 7.8 mm part# 125-0140 Bio-Rad guard cartridge cation H part# 125-0129, Holder part# 125-0131 |
| Method | 0.005M $H_2SO_4$ mobile phase Flow rate: 0.6 ml/min Column temperature: 65° C. RI detector temperature: 55° C. |

The method quantified analyte(s) using calibration standard for ethanol (% w/v). A four point calibration including the origin is used for quantification.

Where applicable, data were analyzed using JMP software (Cary, NC) with Oneway ANOVA of pairs using Tukey-Kramer HSD or Dunnett's. Error bars denoting the 95% confidence level were established by multiplying the standard error of Oneway Anova analysis by 1.96.

TABLE 15

Experimental Plan.
Liquefaction at 85° C. (pH 4.8)

| Alpha-amylase | Dose µg/g DS | Protease | Dose µg/g DS | Glucoamylase | Dose µg/g DS |
|---|---|---|---|---|---|
| 1407 | 1.4 | — | — | — | — |
| 1407 | 1.4 | Pfu | 2 | — | — |
| 1407 | 1.4 | Pfu | 2 | PE001 | 10 |

Table 16 below shows the results:

TABLE 16 below shows the results:

| Treatment | pH | EtOH (% w/v) | EtOH (% Δ) | JMP Std Error | 95% CI |
|---|---|---|---|---|---|
| Control | 4.8 | 9.2 | 100% | 0.022 | 0.042 |
| Pfu | 4.8 | 11.0 | 120% | 0.022 | 0.042 |
| Pfu + PE001 | 4.8 | 11.0 | 120% | 0.022 | 0.042 | cool the liquefied mash temperature from 85° C. down to 32° C. in 7 minutes, and maintain the liquefied mash temperature at 32° C. for 5 minutes. During each run, the mixing was maintained constant at 210 rpm.

Results

An overview of the results is provided in Table 17 and shown in FIGS. 2-5.

Table 17: The doses of enzymes are listed in parentheses for each and are expressed as micro g EP/g DS.

TABLE 17

The doses of enzymes are listed in parentheses for each and are expressed as micro g EP/g DS.

| Experiment No. | Enzyme Description | Peak Viscosity | Average Viscosity Peak-to-Final | Final Viscosity | % Reduction of Peak Viscosity vs. Experiment 2 | % Reduction of Average Viscosity Peak-to-Final vs. Experiment 2 | % Reduction of Final Viscosity vs. Experiment 2 |
|---|---|---|---|---|---|---|---|
| 1 | Alpha-Amylase A (1.4) at pH = 5.8 | 12769 | 535 | 1078 | | | |
| 2 | Alpha-Amylase 1407 (1.4) + Glucoamylase PE001 (10) + Protease 196 (1) at pH = 4.8 | 15050 | 659 | 816 | | | |
| 3 | Alpha-Amylase A (1.4) + Glucoamylase PE001 (10) + Protease 196 (1) at pH = 4.8 | 11848 | 728 | 1831 | | | |
| 4 | Alpha-Amylase A (0.35) + Alpha-Amylase 1407 (1.4) + Glucoamylase PE001 (10) + Protease 196 (1) at pH = 4.8 | 12927 | 527 | 689 | 14% | 20% | 16% |
| 5 | Alpha-Amylase A (0.7) + Alpha-Amylase 1407 (1.4) + Glucoamylase PE001 (10) + Protease 196 (1) at pH = 4.8 | 11454 | 423 | 682 | 24% | 36% | 16% |

Example 10

Improved Lower Viscosity in the Ethanol Production Process

Corn Flour Preparation: Corn flour from Corn LP, Iowa, USA, was sieved and its particle size distribution (PSD) defined. U.S. Standard Test Sieves with ASTM E-11 Specifications for number 12, 16, 20, 30, 40, and 60 sieves were used. The dry-solids (DS) content of the received flour was around 87.4%. Each experimental run was prepared to have the same PSD.

Viscosity Profile Setup and Determination in Rapid Visco Analyzer: A Perten RVA-4 unit was used for measuring the viscosity profile during liquefaction. Corn slurries were prepared for liquefaction by weighing out specified amounts of sieved corn flour into a Perten metal cup that replicated the PSD of the received flour. A 40 gram slurry was made to 32% DS by adding tap water and the pH-adjusted to either 5.80 (Control) using 50% w/w NaOH or 4.80 using 40% v/v $H_2SO_4$. Aliquots of enzyme stock solutions were added prior to each run in the Perten RVA-4 and the amounts were also considered for getting the desired solids. The control slurry used Alpha-Amylase A at pH 5.8. The Perten RVA-4 was programmed to mix the slurry for 1 minute at 25° C., increase the slurry temperature from 25° C. to 85° C. in 6 minutes, hold the temperature at 85° C. constant for 2 hours, The present invention is further described in the following numbered paragraphs:

[1]. A process for producing fermentation products from starch-containing material comprising the steps of:
  i) liquefying the starch-containing material at a pH in the range from 4.5-5.0 at a temperature in the range from 80-90° C. using:
    an alpha-amylase having a T½ (min) at pH 4.5, 85° C., 0.12 mM $CaCl_2$) of at least 10;
    optionally a protease having a thermostability value of more than 20% determined as Relative Activity at 80° C./70° C.;
  ii) saccharifying using a carbohydrate-source generating enzyme;
  iii) fermenting using a fermenting organism.

[2]. The process of paragraph [1], further comprises, prior to the liquefaction step i), the steps of:
  a) reducing the particle size of the starch-containing material, preferably by dry milling;
  b) forming a slurry comprising the starch-containing material and water.

[3]. The process of paragraph [1] or [2], wherein at least 50%, preferably at least 70%, more preferably at least 80%, especially at least 90% of the starch-containing material fit through a sieve with #6 screen.

[4]. The process of any of paragraphs [1]-[3], wherein the pH during liquefaction is between 4.5-4.8.

[5]. The process of any of paragraphs [1]-[4], wherein the temperature during liquefaction is in the range from 82-88° C., preferably around 85° C.

[6]. The process of any of paragraphs [1]-[5], wherein a jet-cooking step is carried out after liquefaction in step i).

[7]. The process of paragraph [6], wherein the jet-cooking is carried out at a temperature between 110-145° C., preferably 120-140° C., such as 125-135° C., preferably around 130° C. for about 1-15 minutes, preferably for about 3-10 minutes, especially around about 5 minutes.

[8]. The process of any of paragraphs [1]-[7], wherein saccharification and fermentation is carried out sequentially or simultaneously.

[9]. The process of any of paragraphs [1]-[8], wherein saccharification is carried out at a temperature from 20-75° C., preferably from 40-70° C., such as around 60° C., and at a pH between 4 and 5, such as about pH 4.5 or about 4.8.

[10]. The process of any of paragraphs [1]-[9], wherein fermentation or simultaneous saccharification and fermentation (SSF) is carried out carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

[11]. The process of any of paragraphs [1]-[10], wherein the fermentation product is recovered after fermentation, such as by distillation.

[12]. The process of any of paragraphs [1]-[11], wherein the fermentation product is an alcohol, preferably ethanol, especially fuel ethanol, potable ethanol and/or industrial ethanol.

[13]. The process of any of paragraphs [1]-[12], wherein the starch-containing starting material is whole grains.

[14]. The process of any of paragraphs [1]-[13], wherein the starch-containing material is derived from corn, wheat, barley, rye, milo, sago, cassava, manioc, tapioca, sorghum, rice or potatoes.

[15]. The process of any of paragraphs [1]-[14], wherein the fermenting organism is yeast, preferably a strain of *Saccharomyces*, especially a strain of *Saccharomyces cerevisae*.

[16]. The process of any of paragraphs [1]-[15], wherein the alpha-amylase has a T½ (min) at pH 4.5, 85° C., 0.12 mM $CaCl_2$) of at least 10, such as at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

[17]. The process of any of paragraphs [1]-[16], wherein the alpha-amylase is a bacterial alpha-amylase.

[18]. The process of paragraph [17], wherein the bacterial alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular the *Bacillus stearothermophilus* alpha-amylase is truncated, preferably to have around 491 amino acids.

[19]. The process of any of paragraphs [1]-[18], wherein the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

[20]. The process of any of paragraphs [1]-[19], wherein the alpha-amylase is derived from *Bacillus stearothermophilus* alpha-amylase truncated to have around 491 amino acids with the mutations selected from the group consisting of:

I181*+G182*+N193F+V59A+Q89R+E129V+K177L+R179E+H208Y+K220P+N224L+Q254S;
I181*+G182*+N193F+E129V+K177L+R179E; and
I181*+G182*+N193F+E129V+K177L+R179E+K220P+N224L+S242Q+Q254S.

[21]. The process of any of paragraphs [1]-[20], wherein a second alpha-amylase is added during liquefaction step i).

[22]. The process of paragraph [21], wherein the second alpha-amylase is of bacterial origin.

[23]. The process of paragraph [21] or [22], wherein the second alpha-amylase is derived from a strain of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular wherein the second alpha-amylase is a truncated *Bacillus stearothermophilus* alpha-amylase, preferably to have around 491 amino acids.

[24]. The process of any of paragraphs [1]-[23], wherein the second alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

[25]. The process of any of paragraphs [21]-[24], wherein the second alpha-amylase has a T½ (min) at pH 4.5, 85° C., 0.12 mM $CaCl_2$) of below 10.

[26]. The process of any of paragraphs [21]-[25], wherein the second alpha-amylase has a T½ (min) at pH 4.5, 85° C., 0.12 mM $CaCl_2$) of below 8, such as below 7, such as below 6, such as below 5.

[27]. The process of any of paragraphs [21]-[26], wherein the second alpha-amylase has a T½ (min) at pH 4.5, 85° C., 0.12 mM $CaCl_2$) between 2 and 10, such as between 3 and 8, such as above 4 to 10, such as above 4 to 8.

[28]. The process of any of paragraphs [21]-[27], wherein the second alpha-amylase is derived from *Bacillus stearothermophilus* and has the following mutations I181*+G182* or I181*+G182*+N193F (using SEQ ID NO: 1 for numbering).

[29]. The process of any of paragraphs [1]-[28], comprising the steps of:
  i) liquefying the starch-containing material at a pH in the range from 4.5-5.0 at a temperature in the range from 80-90° C. using:
     an alpha-amylase having a T½ (min) at pH 4.5, 85° C., 0.12 mM $CaCl_2$) of at least 10, in particular an alpha-amylase of any one paragraphs 16-20 and further a second alpha-amylase having a T½ (min) at pH 4.5, 85° C., 0.12 mM $CaCl_2$) of less than 10, in particular a second alpha-amylase of any one of paragraphs 21-28;
     a protease having a thermostability value of more than 20% determined as Relative Activity at 80° C./70° C.;
  ii) saccharifying using a glucoamylase;
  iii) fermenting using a fermenting organism.

[30]. The process of any of paragraphs [1]-[29], wherein the protease has a thermostability of more than 30%, more than 40%, more than 50%, more than 60%, more than 70%, more than 80%, more than 90% more than 100%, such as more than 105%, such as more than 110%, such as more than 115%, such as more than 120% determined as Relative Activity at 80° C./70° C.

[31]. The process of any of paragraphs [1]-[30], wherein the protease has a thermostability between 50 and 115%, such as between 50 and 70%, such as between 50 and 60%, such as between 100 and 120%, such as between 105 and 115% determined as Relative Activity at 80° C./70° C.

[32]. The process of any of paragraphs [1]-[31], wherein the protease has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

[33]. The process of any of paragraphs [1]-[32], which protease variant has a thermostability between 10 and 50%, such as between 10 and 30%, such as between 10 and 25% determined as Relative Activity at 85° C./70° C.

[34]. The process of any of paragraphs [1]-[33], wherein the thermostability of the protease is between 50 and 110%, such as between 70 and 110%, such as between 90 and 110% determined as Relative Activity at 85° C./70° C.

[35]. The process of any of paragraphs [1]-[34], wherein the protease is fungal organism.

[36]. The process of any of paragraph [1]-[35], wherein the protease is a variant of the metallo protease derived from a strain of the genus *Thermoascus*, preferably a strain of *Thermoascus aurantiacus*, especially *Thermoascus aurantiacus* CGMCC No. 0670.

[37]. The process of any of paragraphs [1]-[36], wherein the protease is a variant of the metallo protease disclosed as the mature part of SEQ ID NO. 2 disclosed in WO 2003/048353 or the mature part of SEQ ID NO: 1 in WO 2010/008841 or SEQ ID NO: 3 herein.

[38]. The process of any of paragraphs [1]-[37], wherein the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 3 herein.

[39]. The process of any of paragraphs [1]-[38], wherein the protease is a variant of the *Thermoascus aurantiacus* protease shown in SEQ ID NO: 3 with the mutations selected from the group consisting of:
  A27K+D79L+Y82F+S87G+D104P+A112P+A126V+ D142L.
  D79L+Y82F+S87G+A112P+D142L;
  Y82F+S87G+S70V+D79L+D104P+A112P+D142L;
  Y82F+S87G+D79L+D104P+A112P+A126V+D142L;
  and

[40]. The process of any of paragraphs [1]-[39], wherein the protease is of bacterial origin.

[41]. The process of any of paragraphs [1]-[40], wherein the protease is derived from a strain of *Pyrococcus*, preferably a strain of *Pyrococcus furiosus*.

[42]. The process of any of paragraphs [1]-[41] wherein the protease is the one shown in SEQ ID NO: 1 in U.S. Pat. No. 6,258,726 or SEQ ID NO: 13 herein.

[43]. The process of any of paragraphs [1]-[42], wherein the protease is one having at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,258,726 or SEQ ID NO: 13 herein.

[44]. The process of any of paragraphs [1]-[43], further wherein a carbohydrate-source generating enzyme is present and/or added during liquefaction step i).

[45]. The process of paragraph [44], wherein the carbohydrate-source generating enzyme present and/or added during liquefaction step i) is a glucoamylase.

[46]. The process of paragraph [44] or [45], wherein the carbohydrate-source generating enzyme is a glucoamylase having a heat stability at 85° C., pH 5.3, of at least 30%, preferably at least 35%.

[47]. The process of any of paragraphs [44]-[46], wherein the carbohydrate-generating enzyme is a glucoamylase having a relative activity at pH 4.5 of at least 80%, preferably at least 85%, preferably at least 90%.

[48]. The process of any of paragraphs [44]-[47], wherein the carbohydrate-generating enzyme is a glucoamylase having a pH stability at pH 4.5 of at least at least 80%, at least 85%, at least 90%, at least 95%, at least 100%.

[49]. The process of any of paragraphs [44]-[48], wherein the carbohydrate-source generating enzyme is a glucoamylase, preferably derived from a strain of the genus *Penicillium*, especially a strain of *Penicillium oxalicum* disclosed as SEQ ID NO: 2 in PCT/CN10/071753 published as WO 2011/127802 or SEQ ID NO: 9 or 14 herein.

[50]. The process of any of paragraphs [44]-[49], wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/ 071753 published as WO 2011/127802 or SEQ ID NO: 9 or 14 herein, or wherein the carbohydrate-source generating enzyme is a variant of the glucoamylase derived from a strain of *Penicillium oxalicum* having a K79V substitution in SEQ ID NO: 9 or 14 (using the mature sequence shown in SEQ ID NO: 14 for numbering).

[51]. The process of any of paragraphs [1]-[50], further wherein a glucoamylase is present and/or added during saccharification and/or fermentation.

[52]. The process of any of paragraphs [1]-[51], wherein the glucoamylase present and/or added during saccharification and/or fermentation is of fungal origin, preferably from a strain of *Aspergillus*, preferably *A. niger*, *A. awamori*, or *A. oryzae*; or a strain of *Trichoderma*, preferably *T. reesei*; or a strain of *Talaromyces*, preferably *T. emersonii*, or a strain of *Pycnoporus*, or a strain of *Gloephyllum*.

[53]. The process of any of paragraphs [1]-[52], further wherein a pullulanase is present during liquefaction and/or saccharification.

[54]. The process of paragraph [53], wherein the pullulanase present or added during liquefaction step i) is a family GH57 pullulanase, wherein the pullulanase preferably includes an X47 domain as disclosed in U.S. 61/289,040 published as WO 2011/087836 or shown in SEQ ID NO: 12 herein.

[55]. The process of paragraph [53] or [54], wherein the pullulanase is derived from a strain from the genus *Thermococcus*, including *Thermococcus litoralis* and *Thermococcus hydrothermalis* or a hybrid thereof.

[56]. The process of any of paragraphs [53]-[55], wherein the pullulanase is the truncated *Thermococcus hydrothermalis* pullulanase at site X4 or a *T. hydrothermalis/T. litoralis* hybrid enzyme with truncation site X4 disclosed in U.S. 61/289,040 published as WO 2011/087836 or shown in SEQID NO: 12 herein.

[57]. The process of any of paragraphs [1]-[56], comprising the steps of:
  i) liquefying the starch-containing material at a pH in the range from 4.5-5.0 at a temperature in the range from 80-90° C. using:
    an alpha-amylase derived from *Bacillus stearothermophilus* having a T½ (min) at pH 4.5, 85° C., 0.12 mM CaCl$_2$) of at least 10;
    a protease having a thermostability value of more than 20% determined as Relative Activity at 80° C./70° C. derived from *Pyrococcus furiosus* or *Thermoascus aurantiacus*;
  ii) saccharifying using a glucoamylase enzyme;
  iii) fermenting using a fermenting organism.

[58]. A composition comprising an alpha-amylase and a protease, wherein the
  i) alpha-amylase has a T½ (min) at pH 4.5, 85° C., 0.12 mM CaCl$_2$) of at least 10;
  ii) protease having a thermostability value of more than 20% determined as Relative Activity at 80° C./70° C.

[59]. The composition of paragraph [58], further comprising a carbohydrate-source generating enzyme.

[60]. The composition of paragraph [58] or [59], wherein the carbohydrate-source generating enzyme is a glucoamylase having a Relative Activity heat stability at 85° C. of at least 20%, at least 30%, preferably at least 35%.

[61]. The composition of any of paragraphs [58]-[60], wherein the alpha-amylase is a bacterial alpha-amylase, in particular of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular wherein the *Bacillus stearothermophilus* alpha-amylase variant is truncated, preferably to have around 491 amino acids.

[62]. The process of any of paragraphs [58]-[61], wherein the alpha-amylase variant has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 3 disclosed in WO 99/019467 or SEQ ID NO: 1 herein.

[63]. The composition of any of paragraphs [58]-[62], wherein the alpha-amylase is derived from *Bacillus stearothermophilus* alpha-amylase truncated to have around 491 amino acids with the mutations selected from the group consisting of:
  I181*+G182*+N193F+V59A+Q89R+E129V+K177L+R179E+H208Y+K220P+N224L+Q254S;
  I181*+G182*+N193F+E129V+K177L+R179E; and
  I181*+G182*+N193F+E129V+K177L+R179E+K220P+N224L+S242Q+Q254S.

[64]. The composition of any of paragraphs [58]-[63], wherein the alpha-amylase has a T % (min) at pH 4.5, 85° C., 0.12 mM CaCl$_2$) of at least 15, such as at least 20, such as at least 25, such as at least 30, such as at least 40, such as at least 50, such as at least 60, such as between 10-70, such as between 15-70, such as between 20-70, such as between 25-70, such as between 30-70, such as between 40-70, such as between 50-70, such as between 60-70.

[65]. The composition of any of paragraphs [58]-[64], further wherein the composition comprises a second alpha-amylase, in particular of bacterial origin.

[66]. The composition of paragraph [65], wherein the second alpha-amylase is derived from a strain of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 1 herein, in particular wherein the second alpha-amylase is a truncated *Bacillus stearothermophilus* alpha-amylase, preferably to have around 491 amino acids.

[67]. The process of any of paragraphs [58]-[66], wherein the second alpha-amylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or at least 100% identity to the mature part of the polypeptide of SEQ ID NO: 3 disclosed in WO 99/019467 or SEQ ID NO: 1 herein.

[68]. The composition of any of paragraphs [65]-[67], wherein the second alpha-amylase has a T½ (min) at pH 4.5, 85° C., 0.12 mM CaCl$_2$) of below 10.

[69]. The composition of any of paragraphs [65]-[68], wherein the second alpha-amylase has a T½ (min) at pH 4.5, 85° C., 0.12 mM CaCl$_2$) of below 8, such as below 7, such as below 6, such as below 5.

[70]. The composition of any of paragraphs [65]-[69], wherein the second alpha-amylase has a T½ (min) at pH 4.5, 85° C., 0.12 mM CaCl$_2$) between 2 and 10, such as between 3 and 8, such as above 4 to 10, such as above 4 to 8.

[71]. The composition of paragraph [64]-[70], wherein the second alpha-amylase is derived from *Bacillus stearothermophilus* and has the following mutations I181*+G182* or I181*+G182*+N193F (using SEQ ID NO: 1 for numbering).

[72]. The composition of any of paragraphs [58]-[71], comprising:
  an alpha-amylase having a T½ (min) at pH 4.5, 85° C., 0.12 mM CaCl$_2$) of at least 10;
  a second alpha-amylase having a T½ (min) at pH 4.5, 85° C., 0.12 mM CaCl$_2$) of less than 10;
  a protease having a thermostability value of more than 20% determined as Relative Activity at 80° C./70° C.;
  a thermostable glucoamylase.

[73]. The composition of paragraph [72], wherein the thermostable alpha-amylase is one of any of paragraphs 61-64.

[74]. The composition of paragraph [72] or [73], wherein the second alpha-amylase is one of any of paragraphs 65-71.

[75]. The composition of any of paragraphs [58]-[74], wherein the protease has a thermostability of more than 30%, more than 40%, more than 50%, more than 60%, more than 70%, more than 80%, more than 90% more than 100%, such as more that 105%, such as more than 110%, such as more than 115%, such as more than 120% determined as Relative Activity at 80° C./70° C.

[76]. The composition of any of paragraphs [58]-[75], wherein the protease has a thermostability between 50 and 115%, such as between 50 and 70%, such as between 50 and 60%, such as between 100 and 120%, such as between 105 and 115% determined as Relative Activity at 80° C./70° C.

[77]. The composition of any of paragraphs [58]-[76], wherein the protease has a thermostability of more than 12%, more than 14%, more than 16%, more than 18%, more than 20%, more than 25%, more than 30%, more than 40%, more that 50%, more than 60%, more than 70%, more than 80%, more than 90%, more than 100%, more than 110% determined as Relative Activity at 85° C./70° C.

[78]. The composition of any of paragraphs [58]-[77], wherein the protease has a thermostability of between 10 and 50%, such as between 10 and 30%, such as between 10 and 25% determined as Relative Activity at 85° C./70° C.

[79]. The composition of any of paragraphs [58]-[78], wherein the protease has a thermostability between 50 and 110%, such as between 70 and 110%, such as between 90 and 110% determined as Relative Activity at 85° C./70° C.
[80]. The composition of any of paragraphs [58]-[79], wherein the protease is a variant of the metallo protease derived from *Thermoascus aurantiacus* CGMCC No. 0670 show in SEQ ID NO: 3 herein.
[81]. The composition of any of paragraphs [58]-[80], wherein the protease variant of the *Thermoascus aurantiacus* protease shown in SEQ ID NO: 3 with the mutations selected from the group consisting of:

A27K+D79L+Y82F+S87G+D104P+A112P+A126V+ D142L;
D79L+Y82F+S87G+A112P+D142L;
Y82F+S87G+S70V+D79L+D104P+A112P+D142L; and
Y82F+S87G+D79L+D104P+A112P+A126V+D142L.

[82]. The composition of any of paragraphs [58]-[81], wherein the protease is derived from a strain of *Pyrococcus*, preferably a strain of *Pyrococcus furiosus*.
[83]. The composition of any of paragraphs [58]-[82], wherein the protease is the one shown in SEQ ID NO: 1 in U.S. Pat. No. 6,258,726 or SEQ ID NO: 13 herein.
[84]. The composition of any of paragraphs [58]-[83], wherein the protease is one having at least 80%, such as at least 85%, such as at least 90%, such as at least 95%, such as at least 96%, such as at least 97%, such as at least 98%, such as at least 99% identity to SEQ ID NO: 1 in U.S. Pat. No. 6,258,726 or SEQ ID NO: 13 herein.
[85]. The composition of any of paragraphs [58]-[84], further comprising a carbohydrate-source generating enzyme, in particular a glucoamylase, which has a heat stability at 85° C., pH 5.3, of at least 30%, preferably at least 35%.
[86]. The composition of paragraph [85], wherein the carbohydrate-generating enzyme is a glucoamylase having a relative activity at pH 4.5 of at least 80%, preferably at least 85%, preferably at least 90%.
[87]. The composition of paragraph [85] or [86], wherein carbohydrate-generating enzyme is a glucoamylase having a pH stability at pH 4.5 of at least at least 80%, at least 85%, at least 90%, at least 95%, at least 100%.
[88]. The composition of any of paragraphs [85]-[87], wherein the carbohydrate-source generating enzyme is a glucoamylase, preferably derived from a strain of the genus *Penicillium*, especially a strain of *Penicillium oxalicum* disclosed as SEQ ID NO: 2 in PCT/CN10/071753 published as WO 2011/127802 or SEQ ID NO: 9 or 14 herein.
[89]. The composition of any of paragraphs [85]-[88], wherein the carbohydrate-source generating enzyme is a variant of the glucoamylase derived from a strain of *Penicillium oxalicum* disclosed as SEQ ID NO: 2 in WO 2011/127802 having a K79V substitution in SEQ ID NO: 9 or 14 (using the mature sequence shown in SEQ ID NO: 14 for numbering).
[90]. The composition of any of paragraphs [85]-[89], wherein the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in PCT/CN10/071753 published as WO 2011/127802 or shown in SEQ ID NO: 9 or 14 herein.
[91]. The composition of paragraphs [58]-[90], further comprising a pullulanase.
[92]. The composition of paragraph [91], wherein the pullulanase is a GH57 pullulanase, which preferably includes an X47 domain as disclosed in U.S. 61/289,040 published as WO 2011/087836.
[93]. The composition of paragraph [91] or [92], wherein the pullulanase is derived from a strain from the genus *Thermococcus*, including *Thermococcus litoralis* and *Thermococcus hydrothermalis* shown in SEQ ID NO: 10 herein, or a hybrid thereof.
[94]. The composition of paragraph [93], wherein the pullulanase is the truncated *Thermococcus hydrothermalis* pullulanase at site X4 or a *T. hydrothermalis/T. litoralis* hybrid enzyme with truncation site X4 disclosed in U.S. 61/289,040 published as WO 2011/087836 or shown in SEQ ID NO: 12 herein.
[95]. The composition of any of paragraphs [58]-[94] comprising:
  i) an alpha-amylase having a T½ (min) at pH 4.5, 85° C., 0.12 mM CaCl$_2$) of at least 10 derived from *Bacillus stearothermophilus*;
  ii) a protease having a thermostability value of more than 20% determined as Relative Activity at 80° C./70° C. derived from *Pyrococcus furiosus* or *Thermoascus aurantiacus*; and optionally
  iii) a glucoamylase derived from *Penicillium oxalicum*.
[96]. The composition of paragraph [95], wherein the composition further comprising a second alpha-amylase having a T½ (min) at pH 4.5, 85° C., 0.12 mM CaCl$_2$) of less than 10 derived from *Bacillus stearothermophilus*.
[97]. Use of a composition of any of paragraphs [58]-[96] in a liquefaction process.
[98]. The use according to paragraph 97, wherein liquefaction is carried out as defined in any of paragraphs [1]-[57].

The invention claimed is:

1. A process for producing a fermentation product from starch-containing material comprising:
   i) liquefying the starch-containing material at a temperature above the initial gelatinization temperature using:
      an alpha-amylase; and
      a protease having at least 95% sequence identity to the amino acid sequence of SEQ ID NO: 13;
   ii) saccharifying the liquefied material obtained in step i) using a glucoamylase; and
   iii) fermenting the saccharified material obtained in step (ii) using a fermenting organism.

2. The process of claim 1, wherein the alpha-amylase is a variant of a *Bacillus* alpha-amylase.

3. The process of claim 1, wherein the alpha-amylase is a variant of a *Bacillus stearothermophilus* alpha-amylase.

4. The process of claim 1, wherein the alpha-amylase has at least 80%, but less than 100% identity to the mature part of the polypeptide of SEQ ID NO: 1.

5. The process of claim 4, wherein the alpha-amylase is truncated.

6. The process of claim 1, wherein the alpha-amylase is a truncated *Bacillus stearothermophilus* alpha-amylase with the mutations selected from the group consisting of:
   I181*+G182*; and
   I181*+G182*+N193F; wherein each position corresponds to a position in the amino acid sequence set forth in SEQ ID NO: 1.

7. The process of claim 1, wherein the alpha-amylase has a T½ (min) at pH 4.5, 85° C., 0.12 mM CaCl$_2$) of at least 10.

8. The process of claim 1, wherein the alpha-amylase has a T½ (min) at pH 4.5, 85° C., 0.12 mM CaCl2) of at least 15.

9. The process of claim 1, wherein the alpha-amylase has a T½ (min) at pH 4.5, 85° C., 0.12 mM CaCl2) of at least 20.

10. The process of claim 1, wherein the alpha-amylase has a T½ (min) at pH 4.5, 85° C., 0.12 mM CaCl2) of at least 25.

11. The process of claim 1, wherein the alpha-amylase has a T½ (min) at pH 4.5, 85° C., 0.12 mM CaCl2) of at least 30.

12. The process of claim 1, wherein the alpha-amylase has a T½ (min) at pH 4.5, 85° C., 0.12 mM CaCl2) of at least 40.

13. The process of claim 1, wherein the alpha-amylase has a T½ (min) at pH 4.5, 85° C., 0.12 mM CaCl2) of at least 50.

14. The process of claim 1, wherein the alpha-amylase has a T½ (min) at pH 4.5, 85° C., 0.12 mM CaCl2) of at least 60.

15. The process of claim 1, wherein the alpha-amylase has a T½ (min) at pH 4.5, 85° C., 0.12 mM CaCl2) of at least 70.

16. The process of claim 1, wherein the protease has at least 96% sequence identity to the amino acid sequence of SEQ ID NO: 13.

17. The process of claim 1, wherein the protease has as at least 97% sequence identity to the amino acid sequence of SEQ ID NO: 13.

18. The process of claim 1, wherein the protease has as at least 98% sequence identity to the amino acid sequence of SEQ ID NO: 13.

19. The process of claim 1, wherein the protease has as at least 99% sequence identity to the amino acid sequence of SEQ ID NO: 13.

20. The process of claim 1, wherein the protease comprises, consists essentially of, or consists of the amino acid sequence of SEQ ID NO: 13.

* * * * *

UNITED STATES PATENT AND TRADEMARK OFFICE
CERTIFICATE OF CORRECTION

PATENT NO. : 11,840,718 B2
APPLICATION NO. : 18/052080
DATED : December 12, 2023
INVENTOR(S) : Deinhammer et al.

It is certified that error appears in the above-identified patent and that said Letters Patent is hereby corrected as shown below:

In the Claims

Please amend Claims 7-15 and 17-19 as follows:

7. The process of claim 1, wherein the alpha-amylase has a T½ (min) at pH 4.5, 85° C., 0.12 mM $CaCl_2$ of at least 10.
8. The process of claim 1, wherein the alpha-amylase has a T½ (min) at pH 4.5, 85° C., 0.12 mM $CaCl_2$ of at least 15.
9. The process of claim 1, wherein the alpha-amylase has a T½ (min) at pH 4.5, 85° C., 0.12 mM $CaCl_2$ of at least 20.
10. The process of claim 1, wherein the alpha-amylase has a T½ (min) at pH 4.5, 85° C., 0.12 mM $CaCl_2$ of at least 25.
11. The process of claim 1, wherein the alpha-amylase has a T½ (min) at pH 4.5, 85° C., 0.12 mM $CaCl_2$ of at least 30.
12. The process of claim 1, wherein the alpha-amylase has a T½ (min) at pH 4.5, 85° C., 0.12 mM $CaCl_2$ of at least 40.
13. The process of claim 1, wherein the alpha-amylase has a T½ (min) at pH 4.5, 85° C., 0.12 mM $CaCl_2$ of at least 50.
14. The process of claim 1, wherein the alpha-amylase has a T½ (min) at pH 4.5, 85° C., 0.12 mM $CaCl_2$ of at least 60.
15. The process of claim 1, wherein the alpha-amylase has a T½ (min) at pH 4.5, 85° C., 0.12 mM $CaCl_2$ of at least 70.
17. The process of claim 1, wherein the protease has at least 97% sequence identity to the amino acid sequence of SEQ ID NO: 13.
18. The process of claim 1, wherein the protease has at least 98% sequence identity to the amino acid sequence of SEQ ID NO: 13.
19. The process of claim 1, wherein the protease has at least 99% sequence identity to the amino acid sequence of SEQ ID NO: 13.

Signed and Sealed this
Twenty-ninth Day of April, 2025

Coke Morgan Stewart
*Acting Director of the United States Patent and Trademark Office*

SEQUENCE LISTING

```
Sequence total quantity: 14
SEQ ID NO: 1           moltype = AA  length = 515
FEATURE                Location/Qualifiers
REGION                 1..515
                       note = synthetic Construct
source                 1..515
                       mol_type = protein
                       organism = Bacillus stearothermophilus
SEQUENCE: 1
AAPFNGTMMQ YFEWYLPDDG TLWTKVANEA NNLSSLGITA LWLPPAYKGT SRSDVGYGVY    60
DLYDLGEFNQ KGTVRTKYGT KAQYLQAIQA AHAAGMQVYA DVVFDHKGGA DGTEWVDAVE   120
VNPSDRNQEI SGTYQIQAWT KFDPPGRGNT YSSFKWRWYH FDGVDWDESR KLSRIYKFRG   180
IGKAWDWEVD TENGNYDYLM YADLDMDHPE VVTELKNWGK WYVNTTNIDG FRLDAVKHIK   240
FSFFPDWLSY VRSQTGKPLF TVGEYWSYDI NKLHNYITKT NGTMSLFDAP LHNKFYTASK   300
SGGAFDMRTL MTNTLMKDQP TLAVTFVDNH DTEPGQALQS WVDPWFKPLA YAFILTRQEG   360
```

```
YPCVFYGDYY GIPQYNIPSL KSKIDPLLIA RRDYAYGTQH DYLDHSDIIG WTREGVTEKP   420
GSGLAALITD GPGGSKWMYV GKQHAGKVFY DLTGNRSDTV TINSDGWGEF KVNGGSVSVW   480
VPRKTTVSTI ARPITTRPWT GEFVRWTEPR LVAWP                             515

SEQ ID NO: 2            moltype = DNA   length = 1068
FEATURE                 Location/Qualifiers
sig_peptide             1..57
misc_feature            58..534
mat_peptide             535..1068
source                  1..1068
                        mol_type = genomic DNA
                        organism = Thermoascus aurantiacus
CDS                     1..1065
SEQUENCE: 2
atgcggctcg ttgcttccct aacggccttg gtggccttgt ccgtacctgt ctttcccgct    60
gctgtcaacg tgaagcgtgc ttcgtcctac ctggagatca ctctgagcca ggtcagcaac   120
actctgatca aggccgtggt ccagaacact ggtagcgacg agttgtcctt cgttcacctg   180
aacttcttca aggacccegc tcctgtcaaa aaggtatcga tgggtctgaa               240
gtgcagttcg agggcatttt gagccgctac aaatcgactg gcctctctcg tgacgccttt   300
acttatctgg ctcccggaga gtcgtcgag gacgttttg atattgcttc gacttacgat    360
ctgaccagcg gcggccctgt aactatccgt actgagggag ttgttcccta cgccacggct   420
aacagcactg atattgccgg ctacatctca tactcgtcta atgtgttgac cattgatgtc   480
gatggcgccg ctgctgccac tgtctccaag gcaatcactc ctttggaccg ccgcactagg   540
atcagttcct gctccggcag cagacagagc gctcttacta cggctctcag aaacgctgct   600
tctcttgcca acgcagctgc cgacgcggct cagtctggat cagcttcaaa gttcagcgag   660
tacttcaaga ctacttctag ctctacccgc cagaccgtgg ccgcgcgtct tcgggctgtt   720
gcgcgggagg catcttcgtc ttcttcggga gccaccacgt actactgcga cgatcccttac  780
ggctactgtt cctccaacgt cctggcttac accctgcctt catacaacat aatcgccaac   840
tgtgacattt tctatactta cctgccggct ctgaccagta cctgtcacgc tcaggatcaa   900
gcgaccactg cccttcacga gttcacccat gcgcctggcg tctacggcta tggcacggac   960
gacctggcgt atggctacca ggctgcgatg gtgtctcagca gcagccaggc tgtcatgaac  1020
gctgacacct acgctctcta tgcgaatgcc atataccttg gttgctaa               1068

SEQ ID NO: 3            moltype = AA   length = 355
FEATURE                 Location/Qualifiers
source                  1..355
                        mol_type = protein
                        organism = Thermoascus aurantiacus
SEQUENCE: 3
MRLVASLTAL VALSVPVFPA AVNVKRASSY LEITLSQVSN TLIKAVVQNT GSDELSFVHL    60
NFFKDPAPVK KVSVYRDGSE VQFEGILSRY KSTGLSRDAF TYLAPGESVE DVFDIASTYD   120
LTSGGPVTIR TEGVVPYATA NSTDIAGYIS YSSNVLTIDV DGAAAATVSK AITPLDRRTR   180
ISSCSGSRQS ALTTALRNAA SLANAAADAA QSGSASKFSE YFKTTSSSTR QTVAARLRAV   240
AREASSSSSG ATTYYCDDPY GYCSSNVLAY TLPSYNIIAN CDIFYTYLPA LTSTCHAQDQ   300
ATTALHEFTH APGVYSPGTD DLAYGYQAAM GLSSSQAVMN ADTYALYANA IYLGC        355

SEQ ID NO: 4            moltype = DNA   length = 49
FEATURE                 Location/Qualifiers
misc_feature            1..49
                        note = synthetic Construct
source                  1..49
                        mol_type = other DNA
                        organism = synthetic construct
SEQUENCE: 4
aacgacggta cccgggggatc ggatccatgc ggctcgttgc ttccctaac               49

SEQ ID NO: 5            moltype = DNA   length = 48
FEATURE                 Location/Qualifiers
misc_feature            1..48
                        note = synthetic Construct
source                  1..48
                        mol_type = other DNA
                        organism = synthetic construct
SEQUENCE: 5
ctaattacat gatgcggccc ttaattaatt agcaaccaag gtatatgg                 48

SEQ ID NO: 6            moltype = DNA   length = 20
FEATURE                 Location/Qualifiers
misc_feature            1..20
                        note = synthetic Construct
source                  1..20
                        mol_type = other DNA
                        organism = synthetic construct
SEQUENCE: 6
taggagttta gtgaacttgc                                                20

SEQ ID NO: 7            moltype = DNA   length = 18
FEATURE                 Location/Qualifiers
misc_feature            1..18
```

|  | note = synthetic Construct |
| --- | --- |
| source | 1..18 |
|  | mol_type = other DNA |
|  | organism = synthetic construct |

SEQUENCE: 7
```
ttcgagcgtc ccaaaacc                                                 18
```

| SEQ ID NO: 8 | moltype = DNA  length = 1851 |
| --- | --- |
| FEATURE | Location/Qualifiers |
| source | 1..1851 |
|  | mol_type = genomic DNA |
|  | organism = Penicillium oxalicum |
| CDS | 1..1851 |

SEQUENCE: 8
```
atgcgtctca ctctattatc aggtgtagcc ggcgttctct gcgcaggaca gctgacggcg   60
gcgcgtcctg atcccaaggg tgggaatctg acgccgttca tccacaaaga gggcgagcgg  120
tcgctccaag gcatcttgga caatctcggt gggcgaggta agaaaacacc cggcactgcc  180
gcagggttgt ttattgccag tccaaacaca gagaatccaa actattatta tacatggact  240
cgtgactcag ctttgactgc caagtgcttg atcgacctgt tcgaagactc tcgggcaaag  300
tttccaattg accgcaaata cttggaaaca ggaattcggg actacgtgtc gtcccaagca  360
atcctccaga gtgtgtctaa tccttctgga accctgaagg atggctctgg tctgggtgaa  420
cccaagtttg agattgacct gaatcccttt tcgggtgcct gggtcggcc tcagcgggat  480
ggcccagcgc tgcgagcgac cgctatgatc acctacgcca actacctgat atcccatggt  540
cagaaatcgg atgtgtcaca ggtcatgtgg ccgattattg ccaatgatct agcatatgtt  600
ggtcaatact ggaataatac cggatttgac ctgtgggaag aggtggatgg gtcaagcttt  660
ttcacgattg cggtccagca ccgagccctt gttgaaggct cgcaactggc gaaaagctc  720
ggcaagtcct gcgatgcctg tgattctcag cctcccagaa tattgtgttt cctgcagagt  780
ttctggaacg gaaagtacat cacctccaac atcaacacgc aagcaagccg ctctggtatc  840
gacctggact ctgtcctggg aagcattcat acctttgatc ccgaagcagc tgtgacgat   900
gcaactttcc agccttgttc tgcccgcgct ctggcgaaca caaggtcta tgtggattcc  960
ttccgctcta tctacaagat taatgcgggt cttgcagagg gatcggctgc caacgttggc 1020
cgctaccccg aggatgttta ccaaggaggc aatccatggt atctcgccac cctaggcgca 1080
tctgaattgc tttacgacgc cttgtaccag tgggacagac ttggcaaact gaagtctcg  1140
gagacctcgt tgtcattctt caaagacttt gacgcgaccg tgaaaattgg ctcgtactcg 1200
aggaacagca agacctacaa gaaattgacc cagtccatca gtcgtacgc ggacgggttc 1260
atccagttag tgcagcagta cactccttct aatggatcc tggccgagca atacgatcgc 1320
aatacggctg ctcctctctc tgcaaacgat ctgacttggt catttgcctc tttcttgacg 1380
gctacgcaac gccgcgatgc cgtggttcct ccctcctggg gcgcaaagtc ggcaaacaaa 1440
gtcccaacca cttgttcagc ctccccctgtt gtgggtactt ataaggcgcc cacggcaact 1500
ttctcatcca agactaagtg cgtccccgct aaagatattg tgcctatcac gttctacctg 1560
attgagaaca cttactatgg agagaacgtc ttcatgagtg gcaacattac tgcgctgggt 1620
aactgggacg ccaagaaagg cttcccactc accgcaaacc tctacacgca agatcaaaac 1680
ttgtggttcg ccagtgtcga gttcatccca gcaggcacac cctttgagta caagtactac 1740
aaggtcgagc ccaatggcga tattacttgg gagaagggtc ccaaccgggt gttcgtcgct 1800
cccacgggat gcccagttca gcctcactcc aacgacgtgt ggcagttttg a          1851
```

| SEQ ID NO: 9 | moltype = AA  length = 616 |
| --- | --- |
| FEATURE | Location/Qualifiers |
| source | 1..616 |
|  | mol_type = protein |
|  | organism = Penicillium oxalicum |

SEQUENCE: 9
```
MRLTLLSGVA GVLCAGQLTA ARPDPKGGNL TPFIHKEGER SLQGILDNLG GRGKKTPGTA   60
AGLFIASPNT ENPNYYYTWT RDSALTAKCL IDLFEDSRAK FPIDRKYLET GIRDYVSSQA  120
ILQSVSNPSG TLKDGSGLGE PKFEIDLNPF SGAWGRPQRD GPALRATAMI TYANYLISHG  180
QKSDVSQVMW PIIANDLAYV GQYWNNTGFD LWEEVDGSSF FTIAVQHRAL VEGSQLAKKL  240
GKSCDACDSQ PPQILCFLQS FWNGKYITSN INTQASRSGI DLDSVLGSIH TFDPEAACDD  300
ATFQPCSARA LANHKVYVDS FRSIYKINAG LAEGSAANVG RYPEDVYQGG NPWYLATLGA  360
SELLYDALYQ WDRLGKLEVS ETSLSFFKDF DATVKIGSYS RNSKTYKKLT QSIKSYADGF  420
IQLVQQYTPS NGSLAEQYDR NTAAPLSAND LTWSFASFLT ATQRRDAVVP PSWGAKSANK  480
VPTTCSASPV VGTYKAPTAT FSSKTKCVPA KDIVPITFYL IENTYYGENV FMSGNITALG  540
NWDAKKGFPL TANLYTQDQN LWFASVEFIP AGTPFEYKYY KVEPNGDITW EKGPNRVFVA  600
PTGCPVQPHS NDVWQF                                                  616
```

| SEQ ID NO: 10 | moltype = DNA  length = 4014 |
| --- | --- |
| FEATURE | Location/Qualifiers |
| sig_peptide | 1..81 |
| mat_peptide | 82..4014 |
| source | 1..4014 |
|  | mol_type = genomic DNA |
|  | organism = Thermococcus hydrothermalis |
| CDS | 1..4011 |

SEQUENCE: 10
```
atgagggggg tggttgccct cttcattgca attttgatgc ttggaagcat cgttggagcg   60
aacgttaaga gcgttggcgc ggcggagccg aagccgctca acgtcataat agtctggcac  120
cagcaccagc cctactacta cgaccctgtc caggacgtct acaccaggcc ctgggtcagg  180
ctccacgcgc cgaacaacta ctggaagatg gcccactacc tgagccagta cccggaggtt  240
cacgccacca ttgacctctc gggttcgctg atagcccagc ttgccgacta catgaacggc  300
aagaaggaca cctaccagat aatcaccgag aagatagcca cggggaaacc cctcaccgtc  360
```

```
gacgagaagt ggttcatgct ccaggcaccg ggagggttct tcgacaacac catcccctgg   420
aacggtgaac cgataaccga ccccaacggc aacccgataa gggacttctg ggaccgctac   480
acggagctga agaacaagat gctcagcgca aaggccaagt acgcaaactt cgtgactgag   540
agccagaagg tcgctgtgac gaacgagttc acagagcagg actacataga cctagcggtt   600
ctcttcaatc tcgcttggat tgactacaat tacatccacg gccgccgga gttcaaggcc   660
ctctacgaca aggttgacga gggcggctat acaaggcgg acgtcaaaac cgttctcgac   720
gcccagatct ggcttctcaa ccacaccttc gaggagcacg agaagataaa cctcctcctc   780
ggaaacggca acgtcgaggt cacggtcgtt ccctacgccc acccgatagg cccgatactc   840
aacgacttcg gctgggacag cgacttcaac gaccaggtca agaaggccga cgaactgtac   900
aagccgtacc tcggcggctgg caccgcggtt ccaaaaggcg gatgggcggc tgagagcgcc   960
ctcaacgaca aaactctgga gatcctcgcc gagaacggct gggagtgggt catgaccgac  1020
cagatggttc tcgaaagct cggcattgag gaaccgtcg agaactacca caagccctgg  1080
gtggccgagt tcaacggaaa gaagatatac ctcttcccaa gaaatcacga tctaagtgac  1140
agagttggct ttacctacag cggaatgaac cagcagcagg ccgttgagga cttcgtcaac  1200
gagctcctca agctccagaa gcagaactac gatggctcgc tggtttacgt ggtcacgctc  1260
gacggcgaga cccccgtgga gaactacccc tacgacgggg agtcttcct caccgaactc  1320
tacaagaagc tgaccgaact ccaggagcag ggtctcataa gaaccctcac cccgagcgag  1380
tacatccagc tctacggcga caaggccaac aagctcacac ctcggatgat ggagcgcctt  1440
gacctcaccg gagacaacgt taacgccctc ctcaaggccc agagcctcgg cgaactctac  1500
gacatgaccg gcgttaagga ggagatgcag tggcccgaga gcagctggat agacggaacc  1560
ctctccacgt ggataggcga gccccaggag aactacggct ggtactggct ctacatggcc  1620
aggaaggccc ttatggagaa caaggataaa atgagccagg cggactggga gaaggcctac  1680
gagtacctgc tccgcgccga ggcaagcgac tggttctggt ggtacggaag cgaccaggac  1740
agcggccagg actacacctt cgaccgctac ctgaagacct acctctacga gatgtacaag  1800
ctggcaggag tcgagccgcc gagctacctc ttcggcaact acttcccgga cggagagccc  1860
tacaccacga ggggcctggt cggactcaag gacggcgtgga tgaagaactt ctccagcatg  1920
tccccgctgg caaagggcgt gagcgtctat ttcgacggcg aggggataca cttcatagtg  1980
aaagggaacc tggacaggtt cgaggtgagc atctgggaga aggatgagcg cgttggcaac  2040
acgttcaccg gcctccaaga gaagccggac gagttgagct atttcatgtt cccattctca  2100
agggacagcg ttggtctcct cataaccaag cacgtcgtgt acgagaacgg aaaggccgag  2160
atatacggcg ccaccgacta cgagaagagc gagaagcttg gggaagccac cgtcaagaac  2220
acgagcgaag gaatcgaagt cgtccttccc tttgactaca tagaaaaccc ctccgacttc  2280
tacttcgctg tctcgacggt caaagatgga gaccttgagg tgataagcac tcctgtggga  2340
ctcaagctcc ctcaccgaggt caagggagtc gtcatagccg atataaccga cccagaaggc  2400
gacgaccatg ggcccgaaa ctacactttat cccacgacaa aggtcttcaa gccaggtgtt  2460
ttcgacctcc tccgcttcag gatgctcgaa cagacggaga gctacgtcat ggagttctac  2520
ttcaaggacc taggtggtaa cccgtggaac ggacccaacg gcttcagcct ccagataatc  2580
gaggtctacc tcgacttcaa ggacggtgga aacagttcgg ccattaagat gttccccgac  2640
ggaccgggag ccaacgtcaa cctcgacccc gagcatccat gggacgttgc cttcaggata  2700
gcgggctggg actacggaaa cctcatcatc ctgccgaacg gaacggccat ccagggcgag  2760
atgcagattt ccgcagatcc ggttaagaac gccataatag tcaaggttcc aaagaagtac  2820
atcgccataa acgaggacta cggcctctgg ggagacgtcc tcgtcggctc gcaggacggc  2880
tacggcccgg acaagtggag aacgcgcca gtggatggca gcagtggaa gcttggaggt  2940
gcggacccgc aggcagtcat aaacggcgtg gccccgcgcg tcattgatga gctggttccg  3000
cagggctttg aaccgaccca ggaggagcag ctgagcagct acgatgcaaa cgacatgaag  3060
ctcgccactg tcaaggcgct gctactcctc aagcagggca tcgttgtgac cgacccggag  3120
ggagacgagc acgggccggg aacgtacacc tatccgacga caaagttttt caagcccggt  3180
gtttttcgacc tcctcaagtt caaggtgacc gagggaagcg acgactggac gctggagttc  3240
cacttcaaag acctcggtgg aaacccgtgg aacgggccga acggcttcag cctgcagata  3300
atcgaggtat acttcgactt caaggagggc gggaacgtct cggccattaa gatgttcccg  3360
gatgggcccg gaagcaacgt ccgtcttgat ccaaatcacc catgggacct ggcgcttagg  3420
atagccggct gggactacgg aaacctgata attctgcccg acggaaccgc ctaccaaggc  3480
gagatgcaga tttccgcaga tccggttaag aacgccataa tagtcaaggt tccaaagaag  3540
tacctgaaca tatccgacta cggactctac accgccgtca tcgtgggttc caagacgggg  3600
tacggcccgg acaagtggag gccccgtggcc gctgaggccg agcagtggaa gtcggaggc  3660
gcagaccccc aggcggtcat agacaacctc gtaccaaggg tcgttgatga actcgtgccg  3720
gagggcttca agccaacgca ggaggagcag ctgagcagct acgaccttga agaagacc  3780
ctggcgacgg tgctcatggt accgctcgtc aatgggactg gcggcgagga accaacgccg  3840
acggagagcc caacggaaac gacgacaacc acacccagcg aaacaaccac cacaacttca  3900
acgaccaccg gcccaagctc aacgaccacc agcacaccac gcggaggaat ctgcggccca  3960
ggcattatag cgggcctggc cctgataccg ctcctcctca agaggaggaa ctga         4014
```

```
SEQ ID NO: 11      moltype = AA   length = 1337
FEATURE            Location/Qualifiers
source             1..1337
                   mol_type = protein
                   organism = Thermococcus hydrothermalis
SEQUENCE: 11
MRRVVALFIA ILMLGSIVGA NVKSVGAAEP KPLNVIIVWH QHQPYYYDPV QDVYTRPWVR    60
LHAANNYWKM AHYLSQYPEV HATIDLSGSL IAQLADYMNG KKDTYQIITE KIANGEPLTV   120
DEKWFMLQAP GGFFDNTIPW NGEPITDPNG NPIRDFWDRY TELKNKMLSA KAKYANFVTE   180
SQKVAVTNEF TEQDYIDLAV LFNLAWIDYN YITSTPEFKA LYDKVDEGGY TRADVKTVLD   240
AQIWLLNHTF EEHEKINLLL GNGNVEVTVV PYAHPIGPIL NDFGWDSDFN DQVKKADELY   300
KPYLGGGTAV PKGGWAAESA LNDKTLEILA ENGWEWVMTD QMVLGKLGIE GTVENYHKPW   360
VAEFNGKKIY LFPRNHDLSD RVGFTYSGMN QQQAVEDFVN ELLKLQKQNY DGSLVYVVTL   420
DGENPVENYP YDGELFLTEL YKKLTELQEQ GLIRTLTPSE YIQLYGDKAN KLTPRMMERL   480
DLTGDNVNAL LKAQSLGELY DMTGVKEEMQ WPESSWIDGT LSTWIGEPQE NYGWYWLYMA   540
RKALMENKDK MSQADWEKAY EYLLRAEASD WFWWYGSDQD SGQDYTFDRY LKTYLYEMYK   600
LAGVEPPSYL FGNYFPDGEP YTTRGLVGLK DGEMKNFSSM SPLAKGVSVY FDGEGIHFIV   660
```

```
KGNLDRFEVS IWEKDERVGN TFTRLQEKPD ELSYFMFPFS RDSVGLLITK HVVYENGKAE    720
IYGATDYEKS EKLGEATVKN TSEGIEVVLP FDYIENPSDF YFAVSTVKDG DLEVISTPVE    780
LKLPTEVKGV VIADITDPEG DDHGPGNYTY PTDKVFKPGV FDLLRFRMLE QTESYVMEFY    840
FKDLGGNPWN GPNGFSLQII EVYLDFKDGG NSSAIKMFPD GPGANVNLDP EHPWDVAFRI    900
AGWDYGNLII LPNGTAIQGE MQISADPVKN AIIVKVPKKY IAINEDYGLW GDVLVGSQDG    960
YGPDKWRTAA VDAEQWKLGG ADPQAVINGV APRVIDELVP QGFEPTQEEQ LSSYDANDMK   1020
LATVKALLLL KQGIVVTDPE GDDHGPGTYT YPTDKVFKPG VFDLLKFKVT EGSDDWTLEF   1080
HFKDLGGNPW NGPNGFSLQI IEVYFDFKEG GNVSAIKMFP DGPGSNVRLD PNHPWDLALR   1140
IAGWDYGNLI ILPDGTAYQG EMQISADPVK NAIIVKVPKK YLNISDYGLY TAVIVGSQDG   1200
YGPDKWRPVA AEAEQWKLGG ADPQAVIDNL VPRVVDELVP EGFKPTQEEQ LSSYDLEKKT   1260
LATVLMVPLV NGTGGEEPTP TESPTETTTT TPSETTTTTS TTTGPSSTTT STPGGGICGP   1320
GIIAGLALIP LLLKRRN                                                 1337

SEQ ID NO: 12           moltype = AA  length = 809
FEATURE                 Location/Qualifiers
REGION                  1..809
                        note = Hybrid pullulanase of Thermoccus hydrothermalis and
                        Thermococcus litoralis
SIGNAL                  1..27
REGION                  28..809
                        note = synthetic Construct
source                  1..809
                        mol_type = protein
                        organism = synthetic construct
SEQUENCE: 12
MKKPLGKIVA STALLISVAF SSSIASAEEP KPLNVIIVWH QHQPYYYDPI QDIYTRPWVR     60
LHAANNYWKM ANYLSKYPDV HVAIDLSGSL IAQLADYMNG KKDTYQIVTE KIANGEPLTL    120
EDKWFMLQAP GGFFDHTIPW NGEPVADENG NPYREQWDRY AELKDKRNNA FKKYANLPLN    180
EQKVKITAEF TEQDYIDLAV LFNLAWIDYN YIINTPELKA LYDKVDVGGY TKEDVATVLK    240
HQMWLLNHTF EEHEKINYLL GNGNVEVTVV PYAHPIGPLL NDFGWYEDFD AHVKKAHELY    300
KKYLGDNRVE PQGGWAAESA LNDKTLEILT NNGWKWVMTD QMVLDILGIP NTVENYYKPW    360
VAEFNGKKIY LFPRNHDLSD RVGFRYSGMN QYQAVEDFVN ELLKVQKENY DGSLVYVVTL    420
DGENPWEHYP FDGKIFLEEL YKKLTELQKQ GLIRTVTPSE YIQMYGDKAN KLTPRMMERL    480
DLTGDNVNAL LKAQSLGELY DMTGVKEEMQ WPESSWIDGT LSTWIGEPQE NYGWYWLYMA    540
RKALMENKDK MSQADWEKAY EYLLRAEASD WFWWYGSDQD SGQDYTFDRY LKTYLYEMYK    600
LAGVEPPSYL FGNYFPDGEP YTTRGLVGLK DGEMKNFSSM SPLAKGVSVY FDGEGIHFIV    660
KGNLDRFEVS IWEKDERVGN TFTRLQEKPD ELSYFMFPFS RDSVGLLITK HVVYENGKAE    720
IYGATDYEKS EKLGEATVKN TSEGIEVVLP FDYIENPSDF YFAVSTVKDG DLEVISTPVE    780
LKLPTEVKGV VIADITDPEG DDHGPGNYT                                     809

SEQ ID NO: 13           moltype = AA  length = 412
FEATURE                 Location/Qualifiers
REGION                  1..412
                        note = mat_peptide - Pyrococcus furiosus protease (Pfu)
source                  1..412
                        mol_type = protein
                        organism = Pyrococcus furiosus
SEQUENCE: 13
AELEGLDESA AQVMATYVWN LGYDGSGITI GIIDTGIDAS HPDLQGKVIG WVDFVNGRSY     60
PYDDHGHGTH VASIAAGTGA ASNGKYKGMA PGAKLAGIKV LGADGSGSIS TIIKGVEWAV    120
DNKDKYGIKV INLSLGSSQS SDGTDALSQA VNAAWDAGLV VVVAAGNSGP NKYTIGSPAA    180
ASKVITVGAV DKYDVITSFS SRGPTADGRL KPEVVAPGNW IIAARASGTS MGQPINDYYT    240
AAPGTSMATP HVAGIAALLL QAHPSWTPDK VKTALIETAD IVKPDEIADI AYGAGRVNAY    300
KAINYDNYAK LVFTGYVANK GSQTHQFVIS GASFVTATLY WDNANSDLDL YLYDPNGNQV    360
DYSYTAYYGF EKVGYYNPTD GTWTIKVVSY SGSANYQVDV VSDGSLSQPG SS            412

SEQ ID NO: 14           moltype = AA  length = 595
FEATURE                 Location/Qualifiers
REGION                  1..595
                        note = mat_peptide - mature Penicillium oxalicum
                         glucoamylase sequence
source                  1..595
                        mol_type = protein
                        organism = Penicillium oxalicum
SEQUENCE: 14
RPDPKGGNLT PFIHKEGERS LQGILDNLGG RGKKTPGTAA GLFIASPNTE NPNYYYTWTR     60
DSALTAKCLI DLFEDSRAKF PIDRKYLETG IRDYKSSQAI LQSVSNPSGT LKDGSGLGEP    120
KPEIDLNPFS GAWGRPQRDG PALRATAMIT YANYLISHGQ KDSVSQVMWP IIANDLAYVG    180
QYWNNTGFDL WEEVDGSSFF TIAVQHRALV EGSQLAKKLG KSCDACDSQP PQILCFLQSF    240
WNGKYITSNI NTQASRSGID LDSVLGSIHT FDPEAACDDA TFQPCSARAL ANHKVYVDSF    300
RSIYKINAGL AEGSAANVGR YPEDVYQGGN PWYLATLGAS ELLYDALYQW DRLGKLEVSE    360
TSLSFFKDFD ATVKIGSYSR NSKTYKKLTQ SIKSYADGFI QLVQQYTPSN GSLAEQYDRN    420
TAAPLSANDL TWSFASFLTA TQRRDAVVPP SWGAKSANKV PTTCSASPVV GTYKAPTATF    480
SSKTKCVPAK DIVPITFYLI ENTYYGENVF MSGNITALGN WDAKKGFPLT ANLYTQDQNL    540
WFASVEFIPA GTPFEYKYYK VEPNGDITWE KGPNRVFVAP TGCPVQPHSN DVWQF         595
```